United States Patent
Zhou et al.

(10) Patent No.: US 12,216,737 B2
(45) Date of Patent: Feb. 4, 2025

(54) SYSTEMS, METHODS, AND APPARATUSES FOR ACTIVELY AND CONTINUALLY FINE-TUNING CONVOLUTIONAL NEURAL NETWORKS TO REDUCE ANNOTATION REQUIREMENTS

(71) Applicant: Arizona Board of Regents on behalf of Arizona State University, Scottsdale, AZ (US)

(72) Inventors: Zongwei Zhou, Tempe, AZ (US); Jae Shin, Chandler, AZ (US); Jianming Liang, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 361 days.

(21) Appl. No.: 17/698,805

(22) Filed: Mar. 18, 2022

(65) Prior Publication Data
US 2022/0300769 A1    Sep. 22, 2022

Related U.S. Application Data

(60) Provisional application No. 63/163,656, filed on Mar. 19, 2021.

(51) Int. Cl.
G06V 10/82    (2022.01)
G06F 18/21    (2023.01)
(Continued)

(52) U.S. Cl.
CPC ........ *G06F 18/217* (2023.01); *G06F 18/2148* (2023.01); *G06T 7/0012* (2013.01);
(Continued)

(58) Field of Classification Search
CPC . G06F 18/217; G06F 18/2148; G06T 7/0012; G06T 2207/20081;
(Continued)

(56) References Cited

U.S. PATENT DOCUMENTS

2014/0072191 A1* 3/2014 Liang .................. G06T 7/70
382/128
2018/0225820 A1* 8/2018 Liang .................. G06V 10/82
(Continued)

OTHER PUBLICATIONS

Aggarwal, U. et al., "Active learning for imbalanced datasets," Proceedings of the IEEE/CVF Winter Conference on Applications of Computer Vision, 2020, pp. 1428-1437.
(Continued)

*Primary Examiner* — Juan M Guillermety
(74) *Attorney, Agent, or Firm* — Elliott, Ostrander & Preston, P.C.

(57) ABSTRACT

Described herein are systems, methods, and apparatuses for actively and continually fine-tuning convolutional neural networks to reduce annotation requirements, in which the trained networks are then utilized in the context of medical imaging. The success of convolutional neural networks (CNNs) in computer vision is largely attributable to the availability of massive annotated datasets, such as ImageNet and Places. However, it is tedious, laborious, and time consuming to create large annotated datasets, and demands costly, specialty-oriented skills. A novel method to naturally integrate active learning and transfer learning (fine-tuning) into a single framework is presented to dramatically reduce annotation cost, starting with a pre-trained CNN to seek "worthy" samples for annotation and gradually enhances the (fine-tuned) CNN via continual fine-tuning. The described method was evaluated using three distinct medical imaging applications, demonstrating that it can reduce annotation efforts by at least half compared with random selection.

15 Claims, 31 Drawing Sheets

(51) Int. Cl.
   *G06F 18/214* (2023.01)
   *G06T 7/00* (2017.01)
   *G06V 10/764* (2022.01)
   *G16H 30/40* (2018.01)

(52) U.S. Cl.
   CPC ............ *G06V 10/764* (2022.01); *G06V 10/82* (2022.01); *G16H 30/40* (2018.01); *G06T 2207/20081* (2013.01); *G06T 2207/20084* (2013.01); *G06T 2207/30032* (2013.01); *G06T 2207/30101* (2013.01); *G06V 2201/032* (2022.01)

(58) Field of Classification Search
   CPC . G06T 2207/20084; G06T 2207/30032; G06T 2207/30101; G06T 2207/10068; G06V 10/764; G06V 10/82; G06V 2201/032; G16H 30/40; G16H 50/20
   See application file for complete search history.

(56) References Cited

U.S. PATENT DOCUMENTS

| | | | | |
|---|---|---|---|---|
| 2018/0314943 | A1* | 11/2018 | Liang | G06V 10/82 |
| 2020/0074701 | A1* | 3/2020 | Liang | G16H 30/40 |
| 2020/0334811 | A1 | 10/2020 | Mansi et al. | |
| 2021/0407076 | A1* | 12/2021 | Wirch | G06F 18/2431 |

OTHER PUBLICATIONS

Ardila, D. et al., "End-to-end lung cancer screening with three-dimensional deep learning on low-dose chest computed tomography," Nature medicine 25.6, 2019, pp. 954-961.
Azizi, S. et al., "Big self-supervised models advance medical image classification," arXiv preprint arXiv:2101.05224, 2021.
Balcan, M.F. et al., "Margin based active learning," International Conference on Computational Learning Theory, 2007, pp. 35-50, Springer Berlin Heidelberg.
Beluch, W.H. et al., "The power of ensembles for active learning in image classification," Proceedings of the IEEE Conference on Computer Vision and Pattern Recognition, 2018, pp. 9368-9377.
Borisov, A. et al., "Active batch learning with stochastic query-by-forest (SQBF)," Active Learning and Experimental Design workshop in conjunction with AISTATS 2010, JMLR Workshop and Conference Proceedings, 2011, pp. 59-69.
Bortsova, G. et al., "Semi-supervised medical image segmentation via learning consistency under transformations," Medical Image Computing and Computer Assisted Intervention—MICCAI 2019: 22nd International Conference, Shenzhen, China, Oct. 13-17, 2019, Proceedings, Part VI 22, 2019, pp. 810-818, Springer International Publishing.
Buda, M. et al., "A systematic study of the class imbalance problem in convolutional neural networks," Neural Networks, 106, 2018, pp. 249-259.
Caron, M. et al., "Unsupervised learning of visual features by contrasting cluster assignments," arXiv preprint arXiv:2006.09882, 2020.
Chakraborty, S. et al., "Active batch selection via convex relaxations with guaranteed solution bounds," IEEE transactions on pattern analysis and machine intelligence, 37.10, 2015, pp. 1945-1958.
Chen, S. et al., "Med3d: Transfer learning for 3d medical image analysis," arXiv preprint arXiv:1904.00625, 2019.
Chen, T. et al., "A simple framework for contrastive learning of visual representations," arXiv preprint arXiv:2002.05709, 2020.
Chen, X. et al., "Exploring simple siamese representation learning," arXiv preprint arXiv:2011.10566, 2021.
Chen, Z. et al., "Lifelong machine learning," Synthesis Lectures on Artificial Intelligence and Machine Learning, 2022, Springer Nature.
Cui, W. et al., "Semi-supervised brain lesion segmentation with an adapted mean teacher model," Information Processing in Medical Imaging: 26th International Conference, IPMI 2019, Hong Kong, China, Jun. 2-7, 2019, Proceedings 26, 2019, pp. 554-565, Springer International Publishing.
Culotta, A. et al., "Reducing labeling effort for structured prediction tasks," AAAI, vol. 5, 2005, pp. 746-751.
Dagan, I. et al. "Committee-based sampling for training probabilistic classifiers," Machine Learning Proceedings, 1995, pp. 150-157, Morgan Kaufmann.
Deng, J. et al., "Imagenet: A large-scale hierarchical image database," 2009 IEEE conference on computer vision and pattern recognition, 2009, pp. 245-255, IEEE.
Ding, Y. et al., "A deep learning model to predict a diagnosis of Alzheimer disease by using 18F-FDG PET of the brain," Radiology, 290.2, 2019, pp. 456-464.
Dosovitskiy, A. et al., "An image is worth 16×16 words: Transformers for image recognition at scale," arXiv preprint arXiv:2010.11929, 2020.
Esteva, A. et al., "A guide to deep learning in healthcare," Nature medicine, 25.1, 2019, pp. 24-29.
Esteva, A. et al., "Dermatologist-level classification of skin cancer with deep neural networks," Nature, 542.7639, 2017, pp. 115-118.
Feng, R. et al., "Parts2whole: Selfsupervised contrastive learning via reconstruction," Domain Adaptation and Representation Transfer, and Distributed and Collaborative Learning: Second MICCAI Workshop, DART 2020, and First MICCAI Workshop, DCL 2020, Held in Conjunction with MICCAI 2020, Lima, Peru, Oct. 4-8, 2020, Proceedings 2, 2020, pp. 85-95, Springer International Publishing.
Fotedar, G. et al., "Extreme consistency: Overcoming annotation scarcity and domain shifts," Medical Image Computing and Computer Assisted Intervention—MICCAI 2020: 23rd International Conference, Lima, Peru, Oct. 4-8, 2020, Proceedings, Part I 23, 2020, pp. 699-709, Springer International Publishing.
Gal, Y. et al., "Deep bayesian active learning with image data," International Conference on Machine Learning, 2017, pp. 1183-1192, PMLR.
Gal, Y. et al., "Dropout as a bayesian approximation: Representing model uncertainty in deep learning," international conference on machine learning, 2016, pp. 1050-1059, PMLR.
Grill, J.B. et al., "Bootstrap your own latent: A new approach to self-supervised learning," arXiv preprint arXiv:2006.07733, 2020.
Guan, Q. et al., "Multi-label chest x-ray image classification via category-wise residual attention learning," Pattern Recognition Letters, 130, 2020, pp. 259-266.
Guendel, S. et al., "Learning to recognize abnormalities in chest x-rays with location-aware dense networks," Progress in Pattern Recognition, Image Analysis, Computer Vision, and Applications: 23rd Iberoamerican Congress, CIARP 2018, Madrid, Spain, Nov. 19-22, 2018, Proceedings 23, 2019, pp. 757-765, Springer International Publishing.
Guyon, I. et al., "Results of the active learning challenge," Active Learning and Experimental Design workshop In conjunction with AISTATS 2010, JMLR Workshop and Conference Proceedings, 2011, pp. 19-45.
Haghighi, F. et al., "Learning semantics-enriched representation via self-discovery, self-classification, and self- restoration," Medical Image Computing and Computer Assisted Intervention—MICCAI 2020: 23rd International Conference, Lima, Peru, Oct. 4-8, 2020, Proceedings, Part I 23, 2020, pp. 137-147, Springer International Publishing.
He, H. et al., "Learning from imbalanced data," IEEE Transactions on knowledge and data engineering, 21.9, 2009, pp. 1263-1284.
He, K. et al., "Deep residual learning for image recognition," Proceedings of the IEEE Conference on Computer Vision and Pattern Recognition, 2016, pp. 770-778.
He, K. et al., "Momentum contrast for unsupervised visual representation learning," Proceedings of the IEEE/CVF Conference on Computer Vision and Pattern Recognition, 2020, pp. 9729-9738.
Hino, H., "Active learning: Problem settings and recent developments," arXiv preprint arXiv:2012.04225, 2020.

(56) References Cited

OTHER PUBLICATIONS

Hinton, G., "How to represent part-whole hierarchies in a neural network," arXiv preprint arXiv:2102.12627, 2023.
Holub, A. et al., "Entropy-based active learning for object recognition," 2008 IEEE Computer Society Conference on Computer Vision and Pattern Recognition Workshops, 2008, pp. 1-8, IEEE.
Huang, G. et al., "Densely connected convolutional networks," Proceedings of the IEEE Conference on Computer Vision and Pattern Recognition, 2017, pp. 4700-4708.
Huang, S.C. et al., "PENet—a scalable deep-learning model for automated diagnosis of pulmonary embolism using volumetric CT imaging." NPJ digital medicine 3.1, 2020.
Irvin, J. et al. "Chexpert: A large chest radiograph dataset with uncertainty labels and expert comparison," Proceedings of the AAAI Conference on Artificial Intelligence, vol. 33, No. 01, 2019, pp. 590-597.
Isensee, F. et al., "nnU-Net: a self-configuring method for deep learning-based biomedical image segmentation," Nature Methods 18.2, 2021, pp. 203-211.
Japkowicz, N. et al., "The class imbalance problem: A systematic study," Intelligent data analysis 6(5), 2002, pp. 429-449.
Käding, C. et al., "Fine-tuning deep neural networks in continuous learning scenarios," Computer Vision—ACCV 2016 Workshops: ACCV 2016 International Workshops, Taipei, Taiwan, Nov. 20-24, 2016, Revised Selected Papers, Part III 13, 2017, pp. 588-605, Springer International Publishing.
Kirkpatrick, J. et al., "Overcoming catastrophic forgetting in neural networks," Proceedings of the national academy of sciences 114.13, 2017, pp. 3521-3526.
Krizhevsky, A. et al., "Imagenet classification with deep convolutional neural networks," Advances in neural information processing systems, 25, 2012, pp. 1097-1105.
Kukar, M., "Transductive reliability estimation for medical diagnosis," Artificial Intelligence in Medicine 29.1-2, 2003, pp. 81-106.
Kulick, J. et al. "Active learning of hyperparameters: An expected cross entropy criterion for active model selection," stat 105, 2014, p. 26.
Kuo, W. et al. "Cost-sensitive active learning for intracranial hemorrhage detection," Medical Image Computing and Computer Assisted Intervention—MICCAI 2018: 21st International Conference, Granada, Spain, Sep. 16-20, 2018, Proceedings, Part III 11, 2018, Springer International Publishing.
Lecun, Y. et al., "Deep learning," nature 521.7553, 2015, pp. 436-444.
Li, X. et al., "Adaptive active learning for image classification," Proceedings of the IEEE Conference on Computer Vision and Pattern Recognition, 2013, pp. 859-866.
Li, X. et al., "Transformation consistent self-ensembling model for semisupervised medical image segmentation," IEEE Transactions on Neural Networks and Learning Systems, 32.2, 2020, pp. 523-534.
Lu, L. et al., "Deep learning and convolutional neural networks for medical image computing," Advances in Computer Vision and Pattern Recognition, 10, 2017, 978-3.
Ma, Y. et al., "Multi-attention network for thoracic disease classification and localization," ICASSP 2019—2019 IEEE International Conference on Acoustics, Speech and Signal Processing (ICASSP), 2019, pp. 1378-1382, IEEE.
Mahapatra, D. et al., "Efficient active learning for image classification and segmentation using a sample selection and conditional generative adversarial network," International Conference on Medical Image Computing and Computer-Assisted Intervention, 2108, pp. 580-588, Springer International Publishing.
McCallum, A.K. et al., Employing EM and Pool-Based Active Learning for Text Classification, ICML, vol. 98, 1998, pp. 350-358.
McCloskey, M. et al., "Catastrophic interference in connectionist networks: The sequential learning problem," Psychology of learning and motivation, vol. 24, 1989, pp. 109-165.
Moen, E. et al. "Deep learning for cellular image analysis," Nature methods, 16.12, 2019, pp. 1233-1246.
Mormont, R. et al., "Comparison of deep transfer learning strategies for digital pathology," Proceedings of the IEEE Conference on Computer Vision and Pattern Recognition Workshops, 2018, pp. 2262-2271.
Mundt, M. et al., "A wholistic view of continual learning with deep neural networks: Forgotten lessons and the bridge to active and open world learning," Neural Networks, 160, 2023, pp. 306-336.
Munjal, P. et al., "Towards robust and reproducible active learning using neural networks," Proceedings of the IEEE/CVF Conference on Computer Vision and Pattern Recognition, 2022, pp. 223-232.
Ozdemir, F. et al., "Active learning for segmentation by optimizing content information for maximal entropy," Deep Learning in Medical Image Analysis and Multimodal Learning for Clinical Decision Support: 4th International Workshop, DLMIA 2018, and 8th International Workshop, ML-CDS 2018, Held in Conjunction with MICCAI 2018, Granada, Spain, Sep. 20, 2018, Proceedings 4, 2018, Springer International Publishing.
Parisi, G.I. et al., "Continual lifelong learning with neural networks: A review," Neural Networks, 113, 2019, pp. 54-71.
Pathak, D. et al., "Context encoders: Feature learning by inpainting," Proceedings of the IEEE Conference on Computer Vision and Pattern Recognition, 2016, pp. 2536-2544.
Purushwalkam, S. et al. "Demystifying contrastive self-supervised learning: Invariances, augmentations and dataset biases," Advances in Neural Information Processing Systems, 33, 2020, pp. 3407-3418.
Ravizza, S. et al., "Predicting the early risk of chronic kidney disease in patients with diabetes using real-world data," Nature medicine, 25(1), 2019, pp. 57-59.
Ren, P. et al., "A survey of deep active learning," ACM computing surveys (CSUR), 54.9, 2021, pp. 1-40.
Sabour, S. et al., "Dynamic routing between capsules," Advances in neural information processing systems, 30, 2017.
Scheffer, T. et al., "Active hidden markov models for information extraction," International Symposium on Intelligent Data Analysis, 2001, pp. 309-218, Springer Berlin Heidelberg.
Sener, O. et al., "Active learning for convolutional neural networks: A core-set approach," arXiv preprint arXiv:1708.00489, 2017.
Settles, B., "Active learning literature survey," 2009, 47 pages.
Shannon, C.E., "A mathematical theory of communication," Bell system technical journal 27.3, 1947, pp. 379-423.
Shao, W. et al., "Deep active learning for nucleus classification in pathology images," 2018 IEEE 15th International Symposium on Biomedical Imaging (ISBI 2018), 2108, pp. 199-202, IEEE.
Shen, D. et al. Image Computing and Computer Assisted Intervention—MICCAI 2019: 22nd International Conference, Shenzhen, China, Oct. 13-17, 2019, Proceedings, Part II, vol. 11765, Springer Nature.
Shui, C. et al., "Deep active learning: Unified and principled method for query and training," International Conference on Artificial Intelligence and Statistics, PMLR, 2020, pp. 1308-1318.
Simonyan, K. et al., "Very deep convolutional networks for large-scale image recognition," arXiv preprint arXiv:1409.1556, 2014.
Sourati, J. et al., "Active deep learning with fisher information for patch-wise semantic segmentation," Deep Learning in Medical Image Analysis, 2018, pp. 83-91, Cham: Springer International Publishing.
Sourati, J. et al., "Classification active learning based on mutual information," Entropy, 18.2, 2016, 51.
Sourati, J. et al., "Intelligent labeling based on fisher information for medical image segmentation using deep learning," IEEE transactions on medical imaging 38.11, 2019, pp. 2642-2653.
Szegedy, C. et al., "Going deeper with convolutions," Proceedings of the IEEE Conference on Computer Vision and Pattern Recognition, 2015, pp. 1-9.
Tajbakhsh, N. et al., "Computer-aided detection and visualization of pulmonary embolism using a novel, compact, and discriminative image representation," Medical image analysis, 58, 2019, 101541.
Tajbakhsh, N. et al., "Computer-aided pulmonary embolism detection using a novel vessel-aligned multi-planar image representation and convolutional neural networks," Medical Image Computing and Computer-Assisted Intervention—MICCAI 2015: 18th International Conference, Munich, Germany, Oct. 5-9, 2015, Proceedings, Part II 18, 2015, pp. 62-69, Springer International Publishing.

(56) References Cited

OTHER PUBLICATIONS

Tajbakhsh, N. et al., "Convolutional neural networks for medical image analysis: Full training or fine tuning?," IEEE transactions on medical imaging, 35.5, 2016, pp. 1299-1312.

Tajbakhsh, N. et al., "Embracing imperfect datasets: A review of deep learning solutions for medical image segmentation," Medical Image Analysis, 63, 2020, 101693.

Tang, Y. et al., "Attention-guided curriculum learning for weakly supervised classification and localization of thoracic diseases on chest radiographs," Machine Learning in Medical Imaging: 9th International Workshop, MLMI 2018, Held in Conjunction with MICCAI 2018, Granada, Spain, Sep. 16, 2018, Proceedings 9, 2018, pp. 249-258, Springer International Publishing.

Touvron, H. et al., "Fixing the train-test resolution discrepancy: FixEfficientNet," arXiv preprint arXiv:2003.08237, 2020.

Tsymbalov, E. et al., "Dropout-based active learning for regression," Analysis of Images, Social Networks and Texts: 7th International Conference, AIST 2018, Moscow, Russia, Jul. 5-7, 2018, Revised Selected Papers 7, 2018, pp. 247-258, Springer International Publishing.

Venturini, L. et al., "Uncertainty estimates as data selection criteria to boost omni-supervised learning," Medical Image Computing and Computer Assisted Intervention—MICCAI 2020: 23rd International Conference, Lima, Peru, Oct. 4-8, 2020, Proceedings, Part I 23, 2020, pp. 689-698, Springer International Publishing.

Wang, W. et al., "Deep active self-paced learning for accurate pulmonary nodule segmentation," Medical Image Computing and Computer Assisted Intervention—MICCAI 2018: 21st International Conference, Granada, Spain, Sep. 16-20, 2018, Proceedings, Part II 11, 2018, pp. 723-731, Springer International Publishing.

Yamamoto, Y. et al., "Automated acquisition of explainable knowledge from unannotated histopathology images," Nature communications, 10.1, 2019, 5642.

Yang, L. et al., Suggestive annotation: A deep active learning framework for biomedical image segmentation. arXiv preprint arXiv: 1706.04737, 2017.

Yu, L. et al., "Uncertainty-aware self-ensembling model for semi-supervised 3D left atrium segmentation," Medical image computing and computer assisted intervention—MICCAI 2019: 22nd international conference, Shenzhen, China, Oct. 13-17, 2019, proceedings, part II 22, 2019, pp. 605-613, Springer International Publishing.

Yuan, M. et al., "Cold-start active learning through self-supervised language modeling," arXiv preprint arXiv:2010.09535, 2020.

Yuan, X.T. et al., "Truncated Power Method for Sparse Eigenvalue Problems," Journal of Machine Learning Research, 14.4, 2013, pp. 899-925.

Zhang, R. et al., "Colorful image colorization," Computer Vision—ECCV 2016: 14th European Conference, Amsterdam, The Netherlands, Oct. 11-14, 2016, Proceedings, Part III 14, 2019, pp. 649-666, Springer International Publishing.

Zhou, B. et al., "Places: A 10 million image database for scene recognition," IEEE transactions on pattern analysis and machine intelligence, 40(6), 2017, pp. 1452-1464.

Zhou, S.K. et al., "Handbook of medical image computing and computer assisted intervention," 2019, Academic Press.

Zhou, Z. et al., "Active, continual fine tuning of convolutional neural networks for reducing annotation efforts," Medical image analysis, 71, 2021, 101997.

Zhou, Z. et al., "Finetuning convolutional neural networks for biomedical image analysis: actively and incrementally," Proceedings of the IEEE Conference on Computer Vision and Pattern Recognition, 2017, pp. 7340-7349.

Zhou, Z. et al., "Integrating active learning and transfer learning for carotid intima-media thickness video interpretation," Journal of digital imaging, 32, 2019, pp. 290-299.

Zhou, Z. et al., "Models genesis," Medical Image Analysis 67, 2021, 101840.

Zhou, Z. et al., "Models genesis: Generic autodidactic models for 3d medical image analysis," Medical Image Computing and Computer Assisted Intervention—MICCAI 2019: 22nd International Conference, Shenzhen, China, Oct. 13-17, 2019, Proceedings, Part IV 22, 2019, pp. 384-393, Springer International Publishing.

Zhu, J. et al., "Rubik's cube+: A self-supervised feature learning framework for 3d medical image analysis," Medical Image Analysis 64, 2020, 101746.

\* cited by examiner

Algorithm #1
195

Algorithm 1: ACFT – Active, continual fine-tuning

Input:
$\mathcal{U} = \{C_i\}$, $i \in [1..n]$ {unlabeled pool $\mathcal{U}$ contains $n$ candidates}
$C_i = \{x_i^j\}$, $j \in [1..m]$ {each $C_i$ contains $m$ patches}
$M_0$: pre-trained CNN; $\alpha$: majority selection ratio; $b$: batch size; $\mathcal{Y}$: category set

Output:
$\mathcal{L}$: labeled candidates; $M_t$: fine-tuned CNN model at Step $t$ 1  $\mathcal{L} \leftarrow \varnothing$; $t \leftarrow 1$
2  repeat
3    for *each $C_i \in \mathcal{U}$* do
4      $p_i \leftarrow M_{t-1}(C_i)$ {outputs of $M_{t-1}$ given $\forall x \in C_i$}
5      $C_i^s \leftarrow C_i$ sorted in descending order according to the predicted dominant class $\hat{y}_i$ by Eq. 3, i.e., $\hat{y}_i = argmax_{y=j} \frac{1}{m} \sum_{j=1}^m p_i^{j,y}$, $\forall i \in [1..\omega b]$
6      $C_i^\alpha \leftarrow$ top $\alpha \times 100\%$ of the patches of the sorted list $C_i^s$
7      Compute $a_i$ for $C_i^\alpha$ by Eq. 2, i.e., $a_i = \lambda_1 e_i + \lambda_2 d_i$
8    end
9    Sort $\mathcal{U}$ according to $a$ in descending order
10   Compute sampling probability $a^s$ using sorted list $a^s$ by Eq. 4, i.e., $a_i^s = (a_i^s - a_{\omega b}^s)/(a_1^s - a_{\omega b}^s)$, $a_i^s = a_i^s/\sum_i a_i^s$
11   Associate labels for $b$ candidates with sampling probabilities: $Q \leftarrow Q(a^s, b)$
12   $P \leftarrow M_{t-1}(\mathcal{L})$ {outputs of $M_{t-1}$ given $\forall x \in \mathcal{L}$}
13   Select misclassified candidates from $\mathcal{L}$ based on their annotation: $\mathcal{H} \leftarrow J(P, \mathcal{L})$
14   Fine-tune $M_{t-1}$ with $\mathcal{H} \cup Q$: $M_t \leftarrow F(\mathcal{H} \cup Q, M_{t-1})$
15   $\mathcal{L} \leftarrow \mathcal{L} \cup Q$, $\mathcal{U} \leftarrow \mathcal{U} \setminus Q$; $t \leftarrow t + 1$
16 until *classification performance in a validation set plateaus*;

FIG. 1E

Table 1
199

| Pattern | Example | + Entropy − Majority | + Entropy + Majority | + Diversity − Majority | + Diversity + Majority |
|---|---|---|---|---|---|
| A | 0.4 0.4 0.4 0.5 0.5 0.5 0.5 0.5 0.6 0.6 0.6 | 7.52 | 2.02 | 4.38 | 0.00 |
| B | 0.0 0.1 0.2 0.3 0.4 0.4 0.6 0.7 0.8 1.0 1.0 | 4.57 | 0.83 | 1237.21 | 20.79 |
| C | 0.0 0.0 0.0 0.1 0.1 0.9 0.9 1.0 1.0 1.0 1.0 | 1.30 | 0.00 | 2816.66 | 0.00 |
| D | 0.0 0.0 0.0 0.0 0.0 0.0 0.0 0.0 1 0.1 0.1 0.1 | 1.30 | 0.00 | 189.54 | 0.00 |
| E | 0.9 0.9 0.9 0.9 1.0 1.0 1.0 1.0 1.0 1.0 1.0 | 1.30 | 0.00 | 189.54 | 0.00 |
| F | 0.0 0.0 0.0 0.0 0.1 0.1 0.1 0.2 0.2 0.3 0.9 1.0 | 3.24 | 0.33 | 1076.87 | 13.54 |
| G | 0.0 0.1 0.7 0.8 0.8 0.9 0.9 0.9 1.0 1.0 1.0 | 3.24 | 0.33 | 1076.87 | 13.54 |

FIG. 1F

Equation #1
205

$$e_i = -\frac{1}{m}\sum_{k=1}^{|\gamma|}\sum_{j=1}^{m} P_i^{j,k} \log P_i^{j,k},$$

$$d_i = \sum_{k=1}^{|\gamma|}\sum_{j=1}^{m}\sum_{l=j}^{m}(P_i^{j,k} - P_i^{l,k})\log\frac{P_i^{j,k}}{P_i^{l,k}}$$

Equation #2
206

$$a_i = \lambda_1 e_i + \lambda_2 d_i$$

Equation #3
207

$$\hat{y}_i = \operatorname*{argmax}_{y \in \mathcal{Y}} \frac{1}{m}\sum_{j=1}^{m} P_i^{j,y}$$

FIG. 2B $$a_i^t = (a_i^t - a_{\omega b}^t)/(a_1^t - a_{\omega b}^t),$$

$$a_i^s = a_i^t / \sum_i a_i^t, \forall i \in [1, \omega b].$$

Equation #4
408

FIG. 4B

Table 2
495

| Code | Description of learning strategy |
|---|---|
| $RFT_{(LQ)}$ | Fine-tuning from $M_0$ using $\mathcal{L}$ and randomly selected $\mathcal{Q}$ |
| $AFT_{(LQ)}$ | Fine-tuning from $M_0$ using $\mathcal{L}$ and actively selected $\mathcal{Q}$ |
| $ACFT_{(Q)}$ | Continual fine-tuning from $M_{t-1}$ using actively selected $\mathcal{Q}$ only |
| $ACFT_{(LQ)}$ | Continual fine-tuning from $M_{t-1}$ using $\mathcal{L}$ and actively selected $\mathcal{Q}$ |
| $ACFT_{(HQ)}$ | Continual fine-tuning from $M_{t-1}$ using $\mathcal{H}$ and actively selected $\mathcal{Q}$ |

1 $\mathcal{L}$: Annotated candidates. 2 $\mathcal{Q}$: Newly annotated candidates. 3 $\mathcal{H}$: Misclassified candidates. 4 $M_0$: Pre-trained CNNs from large scale dataset (like IMAGENET). 5 $M_{t-1}$: Pre-trained CNNs from last active selecting step.

FIG. 4C

| Applications | $\mu$ | $lr$ | $lr_{fs}$ | $\gamma$ | epoch |
|---|---|---|---|---|---|
| Colonoscopy frame classification | 0.9 | 1e-4 | 1e-3 | 0.95 | 8 |
| Polyp detection | 0.9 | 1e-4 | 1e-3 | 0.95 | 10 |
| Pulmonary embolism detection | 0.9 | 1e-3 | 1e-2 | 0.95 | 5 |

Table 3
496

FIG. 4D (a) Colonoscopy Frame Classification (b) Polyp Detection (c) Pulmonary Embolism Detection Table 4
798

| Application | Learning strategy | + Diversity - Majority - Randomness | + Diversity + Majority - Randomness | + Diversity - Majority + Randomness | + Diversity + Majority + Randomness | + Entropy - Majority - Randomness | + Entropy + Majority - Randomness | + Entropy - Majority + Randomness | + Entropy + Majority + Randomness |
|---|---|---|---|---|---|---|---|---|---|
| Colonoscopy frame classification | ACFT$_{(Q)}$ | 0.8375 | 0.8773 | 0.8995 | 0.9160 | 0.8444 | 0.8227 | 0.9136 | 0.9061 |
| | ACFT$_{(JQ)}$ | 0.8501 | 0.8956 | 0.9083 | 0.9262 | 0.9149 | 0.9051 | 0.9033 | 0.9223 |
| | AFT$_{(JQ)}$ | 0.9183 | 0.9253 | 0.9299 | 0.9344 | 0.9219 | 0.9180 | 0.9268 | 0.9291 |
| | ACFT$_{(JSQ)}$ | 0.9048 | 0.9236 | 0.9241 | 0.9179 | 0.9198 | 0.9266 | 0.9257 | 0.9293 |
| Polyp detection | ACFT$_{(Q)}$ | 0.8609 | 0.9023 | 0.8984 | 0.9168 | 0.8834 | 0.8656 | 0.9034 | 0.9271 |
| | ACFT$_{(JQ)}$ | 0.9195 | 0.9142 | 0.9497 | 0.9488 | 0.9204 | 0.9255 | 0.9475 | 0.9444 |
| | AFT$_{(JQ)}$ | 0.9242 | 0.9285 | 0.9353 | 0.9355 | 0.9292 | 0.9238 | 0.9367 | 0.9522* |
| | ACFT$_{(JSQ)}$ | 0.9013 | 0.9370 | 0.9116 | 0.9363 | 0.9321 | 0.9436 | 0.9196 | 0.9443 |
| Pulmonary embolism detection | ACFT$_{(Q)}$ | 0.7828 | 0.7911 | 0.7690 | 0.7977 | 0.7855 | 0.7736 | 0.7296 | 0.7833 |
| | ACFT$_{(JQ)}$ | 0.8083 | 0.8176 | 0.7975 | 0.8263 | 0.8032 | 0.8086 | 0.8022 | 0.8245 |
| | AFT$_{(JQ)}$ | 0.7650 | 0.7973 | 0.7978 | 0.8040 | 0.7917 | 0.7878 | 0.7964 | 0.8222 |
| | ACFT$_{(JSQ)}$ | 0.8272* | 0.7876 | 0.8047 | 0.8245 | 0.8218 | 0.7995 | 0.8155 | 0.8205 |

1 RFT in colonoscopy frame classification: ALC = 0.8958±0.0176  2 RFT in polyp detection: ALC = 0.9358±0.0130  3 RFT in pulmonary embolism detection: ALC = 0.7849±0.0261

FIG. 7C

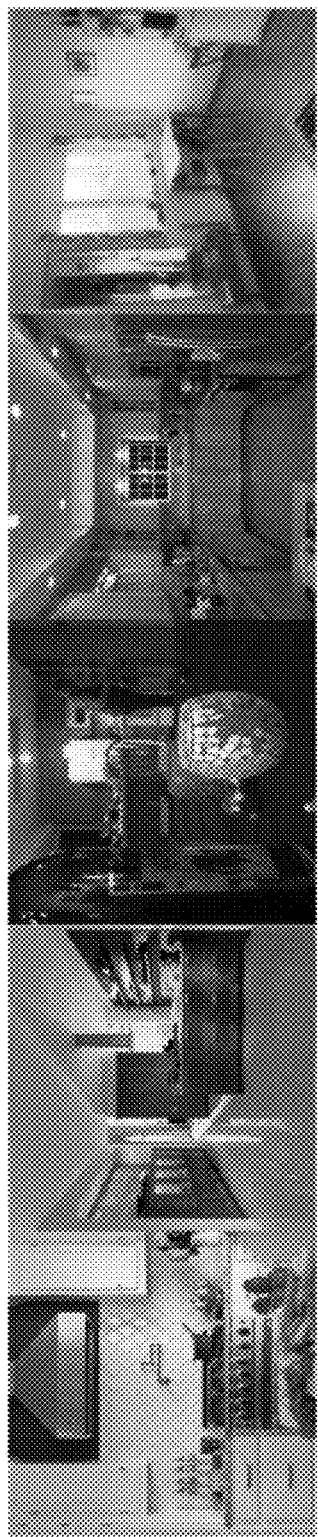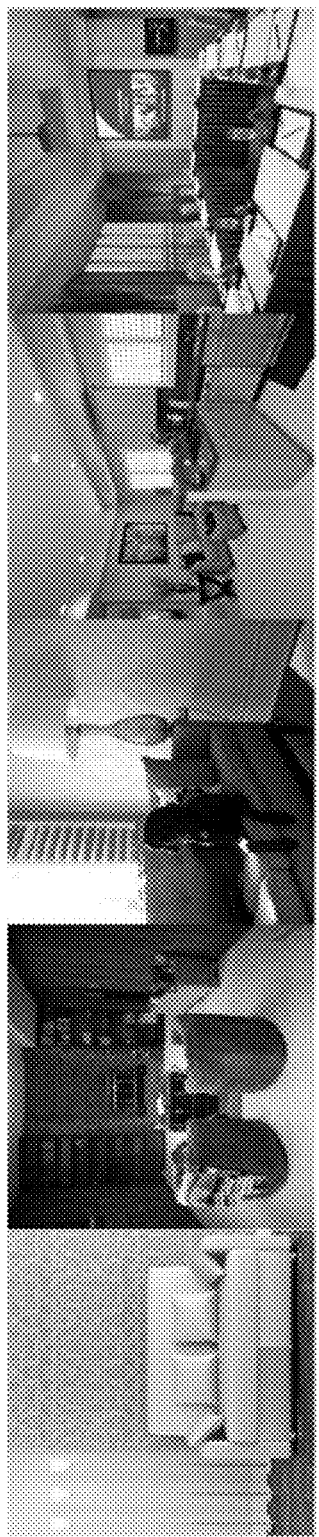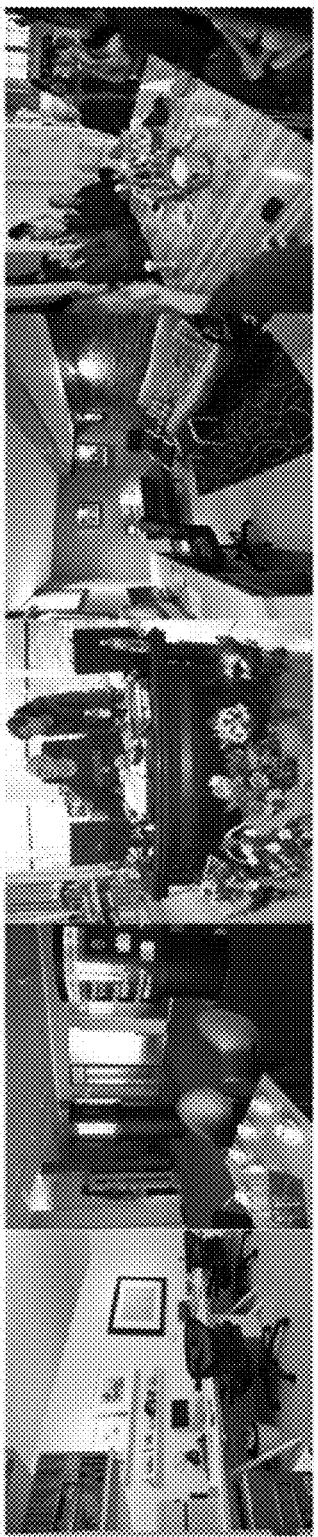
(a) (b) (c)
FIG. 13

SYSTEMS, METHODS, AND APPARATUSES FOR ACTIVELY AND CONTINUALLY FINE-TUNING CONVOLUTIONAL NEURAL NETWORKS TO REDUCE ANNOTATION REQUIREMENTS

CLAIM OF PRIORITY

This non-provisional U.S. Utility Patent Applications is related to, and claims priority to the U.S. Provisional Patent Application No. 63/163,656, entitled "SYSTEMS, METHODS, AND APPARATUSES FOR ACTIVELY AND CONTINUALLY FINE TUNING CONVOLUTIONAL NEURAL NETWORKS TO REDUCE ANNOTATION REQUIREMENTS," filed Mar. 19, 2021, the entire contents of which are incorporated herein by reference as though set forth in full.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for actively and continually fine-tuning convolutional neural networks to reduce annotation requirements, in which trained networks are then utilized for the processing of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Not only is annotating medical images tedious and time-consuming, but it also demands costly, specialty-oriented expertise, which is not easily accessible.

The present state of the art may therefore benefit from the systems, methods, and apparatuses for actively and continually fine-tuning convolutional neural networks to reduce annotation requirements, as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 1E depicts Algorithm #1, for implementing Active Continual Fine-Tuning ("ACFT"), used in accordance with described embodiments;

FIG. 1F depicts Table 1 at element 199, for implementing Active Continual Fine-Tuning ("ACFT"), used in accordance with described embodiments;

FIG. 2B presents equations 1, 2, and 3;

FIG. 4B presents equation 4;

FIG. 4C depicts Table 2, depicting an active learning strategy definition;

FIG. 4D depicts Table 3, listing the earning parameters used for training and fine-tuning of AlexNet for AFT in the described experiments;

FIG. 7C depicts Table 4, providing a comparison of proposed active learning strategies and selection criteria;

FIG. 13 illustrates the ideas behind ACFT by utilizing PLACES-3 for scene classification in natural images.

DETAILED DESCRIPTION

Described herein are systems, methods, and apparatuses for actively and continually fine-tuning convolutional neural networks to reduce annotation requirements, in which the trained networks are then utilized in the context of medical imaging. The success of convolutional neural networks (CNNs) in computer vision is largely attributable to the availability of massive annotated datasets, such as ImageNet and Places. However, in medical imaging, it is challenging to create such large annotated datasets, as annotating medical images is not only tedious, laborious, and time consuming, but it also demands costly, specialty-oriented skills, which are not easily accessible. To dramatically reduce annotation cost, this paper presents a novel method to naturally integrate active learning and transfer learning (fine-tuning) into a single framework, which starts directly with a pre-trained CNN to seek "worthy" samples for annotation and gradually enhances the (fine-tuned) CNN via continual fine-tuning. The method was evaluated using three distinct medical imaging applications, demonstrating that it can reduce annotation efforts by at least half compared with random selection.

Key Highlights of the disclosed ACFT methodologies include at least the following: 1) ACFT dramatically reduces annotation efforts compared with random selection; 2) ACFT selects the most informative and representative samples for annotation; 3) ACFT automatically handles noise labels by computing entropy and diversity locally; 4) ACFT strikes a balance between exploration and exploitation by injecting randomization; and 5) ACFT offers a general solution in both medical and natural imaging.

Figure 1A:
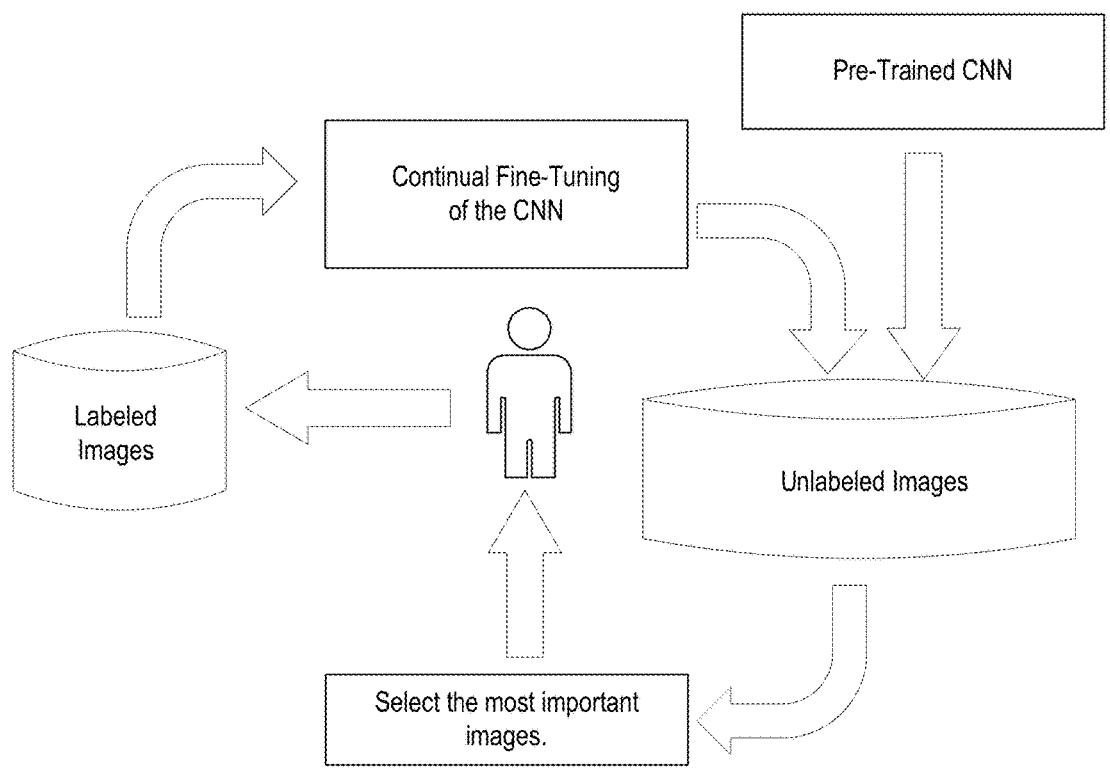
FIG. 1A depicts a method flow for implementing AFCT or "Active Continual Fine-Tuning," in accordance with described embodiments.

Notably, the use of AFCT or "Active Continual Fine-Tuning" (ACFT hereinafter) dramatically reduces annotation efforts when compared with random selection (RFT) techniques, as depicted by each of FIGS. 1A and 1C, as follows:

FIG. 1A depicts a method flow for implementing AFCT or "Active Continual Fine-Tuning," in accordance with described embodiments.

Figure 1B:
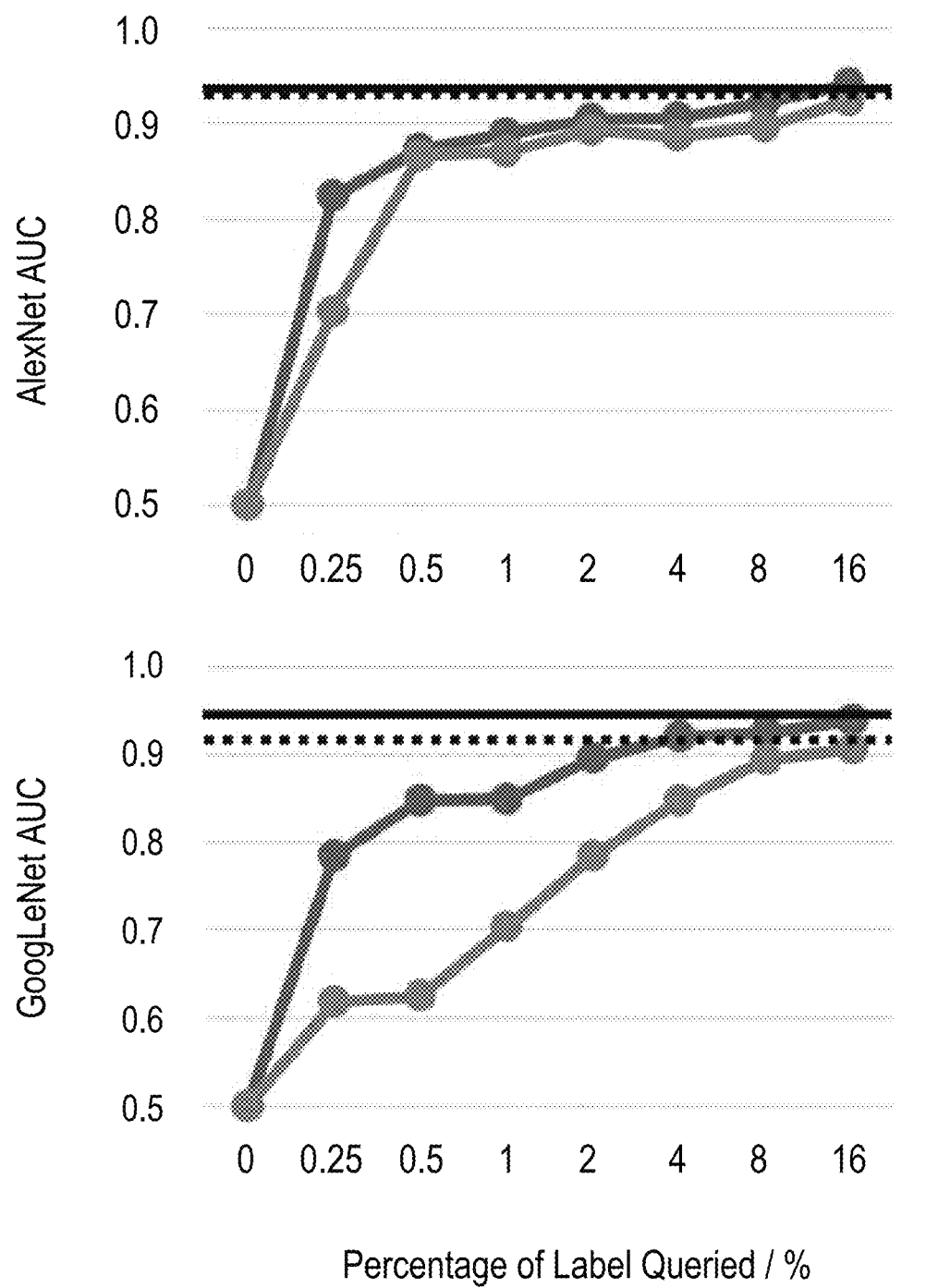
FIGS. 1B, 1C, and 1D depict a comparison of both AFCT and RFT methodologies as applied via AlexNet and GoogLeNet for each of colonoscopy frame classification, in accordance with described embodiments.
Figure 1C:
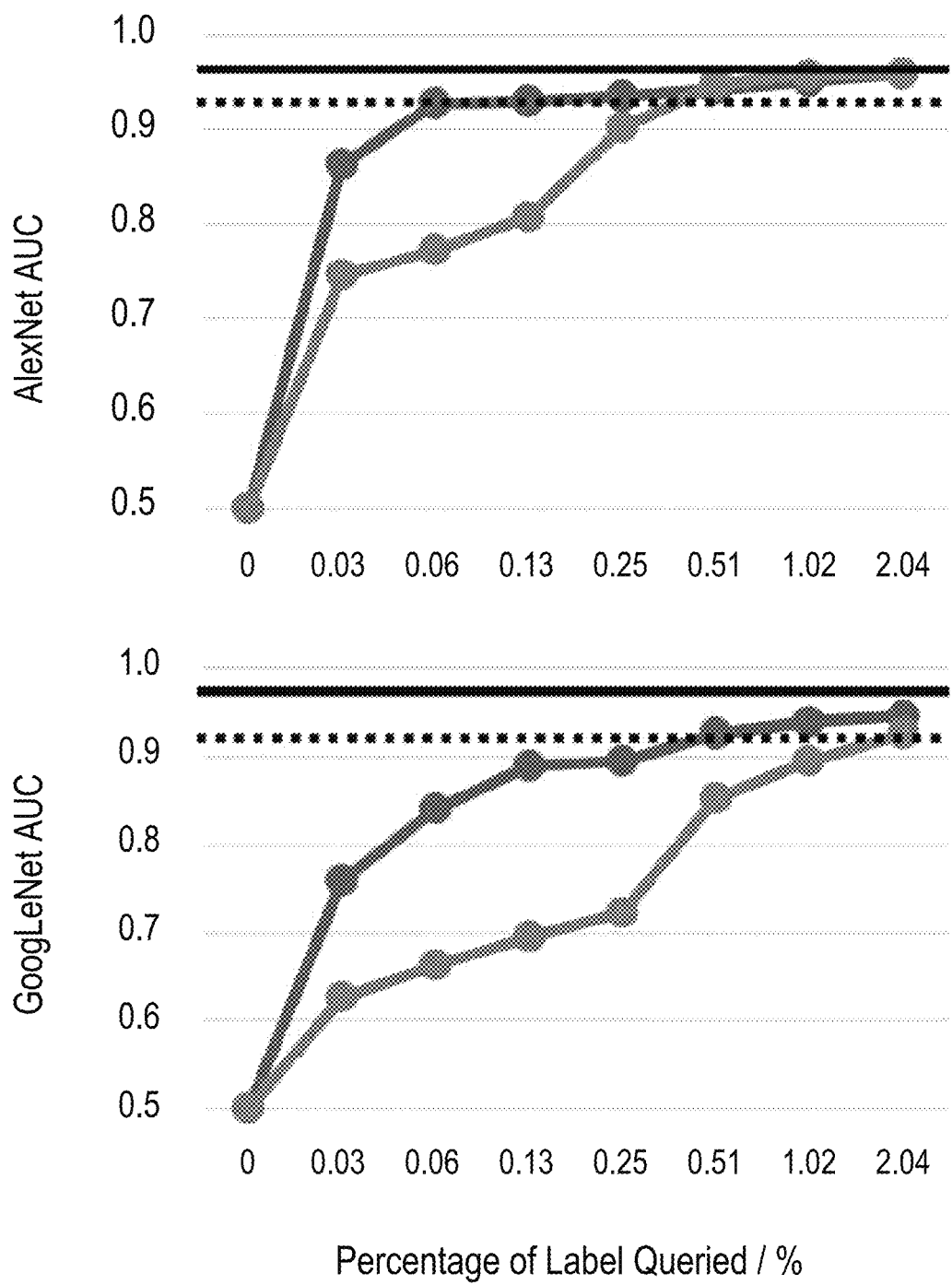
Figure 1D:
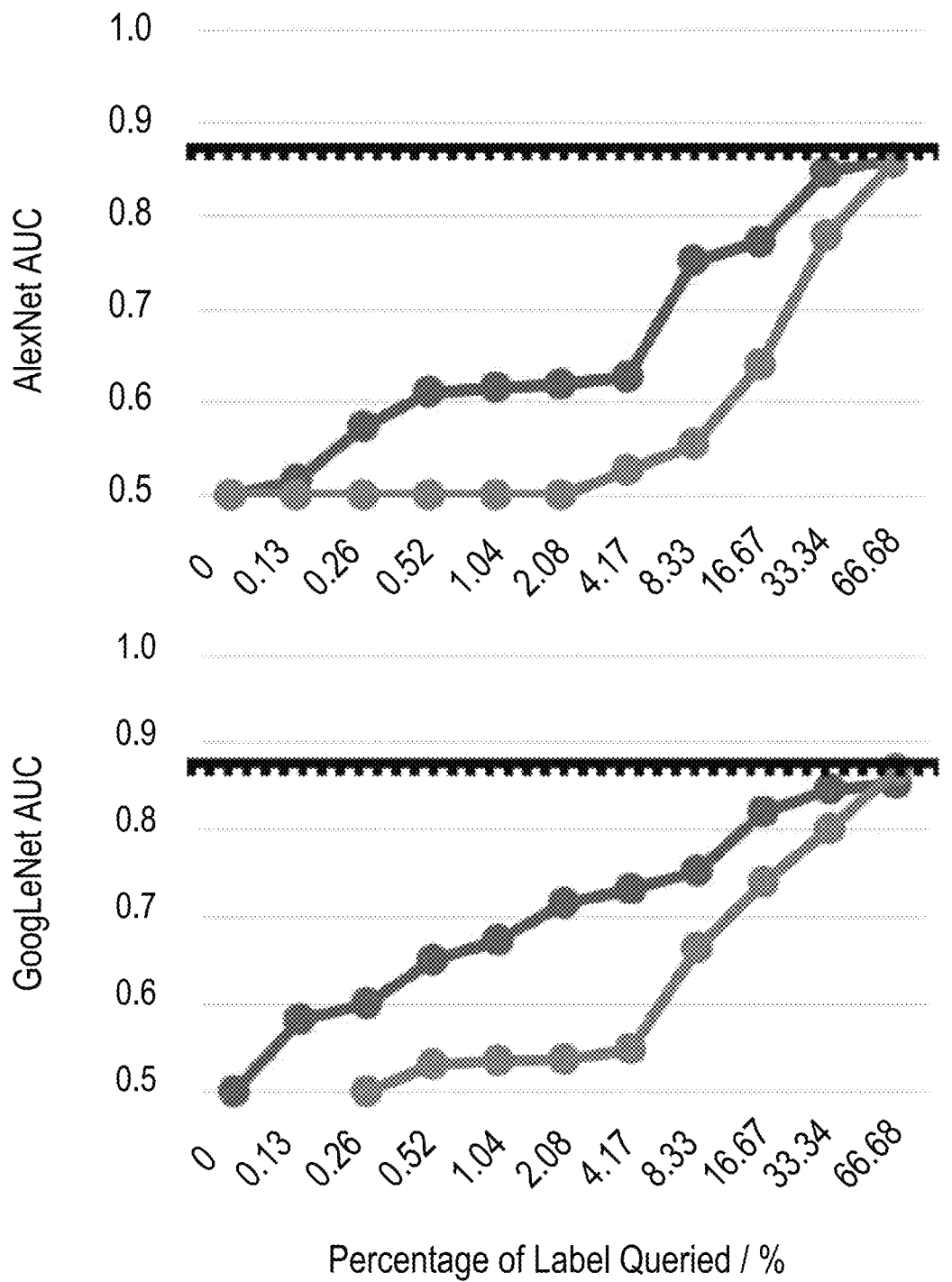

FIGS. 1B, 1C, and 1D depict a comparison of both AFCT and RFT methodologies as applied via AlexNet and GoogLeNet for each of colonoscopy frame classification, (FIG. 1B) polyp detection (FIG. 1C) and pulmonary embolism detection (FIG. 1D). Specifically depicted is the manner in which Active Continual Fine-Tuning (ACFT) dramatically reduces annotation efforts compared with random selection (RFT) methodologies.

INTRODUCTION

Convolutional neural networks (CNNs) have ushered in a revolution in computer vision owing to the use of large annotated datasets, such as ImageNet and Places. As evidenced by recent books and numerous compelling techniques for different imaging tasks, there is widespread and intense interest in applying CNNs to medical image analysis, but the adoption of CNNs in medical imaging is hampered by the lack of such large annotated datasets. Annotating medical images is not only tedious and time consuming, but it also requires costly, specialty-oriented knowledge and skills, which are not readily accessible. Therefore, the inventors sought to answer this critical question: How to dramatically reduce the cost of annotation when applying CNNs to medical imaging? In doing so, a novel method called ACFT (active, continual fine-tuning) was developed to naturally integrate active learning and transfer learning into a single framework. The described ACFT method starts directly with a pre-trained CNN to seek "salient" samples from the un-annotated pool for annotation, and the (fine-tuned) CNN is continually fine-tuned using newly annotated samples combined with all misclassified samples. The method was evaluated in three different applications, including colonoscopy frame classification, polyp detection, and pulmonary embolism (PE) detection, demonstrating that the cost of annotation can be reduced by at least half.

This performance is attributable to a simple yet powerful observation: to boost the performance of CNNs in medical imaging, multiple patches are usually generated automatically for each sample through data augmentation; these patches generated from the same sample share the same label, and are naturally expected to have similar predictions by the current CNN before they are expanded into the training dataset. As a result, their entropy and diversity provide a useful indicator of the "power" of a sample for elevating the performance of the current CNN. However, automatic data augmentation inevitably generates "hard" samples, injecting noisy labels. Therefore, to significantly enhance the robustness of active selection, entropy and diversity were computed from only a portion of the patches according to the majority predictions by the current CNN (refer to the section entitled "Handling noisy labels via majority selection"). Furthermore, to strike a balance between exploration and exploitation, randomness was incorporated into the active selection (refer to the section entitled "Injecting randomization in active selection"); and to prevent catastrophic forgetting, newly selected samples were combined with misclassified samples (refer to the section entitled "Comparison of proposed learning strategies").

FIG. 1E depicts Algorithm #1 at element 195, for implementing Active Continual Fine-Tuning ("ACFT"), in accordance with described embodiments.

Several researchers have demonstrated the utility of fine-tuning CNNs for medical image analysis, but they only performed one-time fine-tuning; that is, simply fine-tuning a pre-trained CNN once with all available training samples, involving no active selection processes. The proposed method is among the first to integrate active learning into fine-tuning CNNs in a continual fashion to make CNNs more amenable to medical image analysis, particularly with the intention of decreasing the efforts of annotation dramatically. Compared with conventional active learning, the method, summarized as Algorithm 1 (see FIG. 1E, element 195), offers at least the following eight advantages:

1. The algorithm starts with a completely empty labeled dataset, requiring no seed-labeled samples (see again Algorithm 1);
2. The algorithm actively selects the most informative and representative samples by naturally exploiting expected consistency among the patches within each sample (refer to the section entitled "Illustrating active candidate selection");
3. The algorithm computes selection criteria locally on a small number of patches within each sample, saving considerable computation time (refer to the section entitled "Seeking worthy candidates");
4. The algorithm automatically handles noisy labels via majority selection (refer to the section entitled "Handling noisy labels via majority selection");
5. The algorithm balances exploration and exploitation by incorporating randomness into active selection (refer to the section entitled "Observations on active selection criteria").
6. The algorithm incrementally improves the learner through continual fine-tuning rather than through repeated retraining (refer to the section entitled "Seeking worthy candidates");
7. The algorithm focuses on hard samples, preventing catastrophic forgetting (refer to the section entitled "Comparison of proposed learning strategies"); and
8. The algorithm autonomously balances training samples among classes (refer to the section entitled "Can actively selected samples be automatically balanced?" and FIG. 8).

More importantly, the disclosed methodology has the potential to positively impact computer-aided diagnosis (CAD) in medical imaging. The current regulations require that CAD systems be deployed in a "closed" environment, in which all CAD results are reviewed and errors, if any, must be corrected by radiologists. As a result, all false positives are dismissed and all false negatives are supplied, an instant on-line feedback process that makes it possible for CAD systems to be self-learning and self-improving after deployment given the continual fine-tuning capability of the described methodology.

Distinctions from Prior Known Techniques and Related Works

Techniques utilizing AIFT (Active, Incremental Fine-Tuning) share some similarity to the described method. However, the AIFT methodology is limited to binary classifications and medical imaging, and used all labeled samples available at each step, thereby demanding extensive training time and substantial computer memory. The current approach set forth herein is a significant extension of the inventors' previous work with several major enhancements: (1) generalization from binary classification to multi-class classification; (2) extension from computer-aided diagnosis in medical imaging to scene classification in natural images; (3) combination of newly selected samples with hard (misclassified) ones, to eliminate easy samples for reducing training time, and to concentrate on hard samples for preventing catastrophic forgetting; (4) injection of randomness to enhance robustness in active selection; (5) extensive experimentation with all reasonable combinations of data and models in search of an optimal strategy; (6) demonstration of consistent annotation reduction using different CNN architectures; and (7) illustration of the active selection process using a gallery of patches associated with predictions.

Transfer learning for medical imaging: Pre-training a model on large-scale image datasets and then fine-tuning it on various target tasks has become a de facto paradigm across many medical specialties. To classify the common thoracic diseases on chest radiography, nearly all the leading approaches follow this paradigm by adopting different architectures along with their weights pre-trained from ImageNet. Other representative medical applications include identifying skin cancer from dermatologist level photographs, diagnosing Alzheimer's Disease from 18F-FDG PET of the brain, and performing effective detection of pulmonary embolism from CTPA. Recent breakthrough in self-supervised pre-training, on the other hand, has led to visual representation that approaches and possibly surpasses what was learned from ImageNet. Self-supervised pre-training has also been adopted for the medical domain, wherein prior solutions develop generic CNNs that are directly pre-trained from medical images, mitigating the mandatory requirement of expert annotation and reducing the large domain gap between natural and medical images. Despite the immense popularity of transfer learning in medical imaging, these works exclusively employed one-time fine-tuning—simply fine-tuning a pre-trained CNN with available training samples for only one time. In real-world applications, instead of training on a still dataset, experts record new samples constantly and expect the samples to be used upon their availability; with the ability to deal with new data, continual learning is the bridge to active and open world learning. Compared with the existing continual learning approaches, the newly devised learning strategy is more amenable to active fine-tuning because it focuses more on the newly annotated samples and also recognizes those misclassified ones, eliminating repeated training on those easy samples in the annotated pool.

Integrating active learning with deep learning: The uncertainty and diversity are the most compelling active selection criteria, which appraise the worthiness of annotating a sample from two different aspects. Uncertainty-based criteria argue that the more uncertain a prediction is, the more value added when including the label of that sample into the training set. Sampling with least confidence, or margin of the prediction has been successful in training models with fewer labels than random sampling. The limitation of uncertainty-based criteria is that some of the selected samples are prone to redundancy and outliers and may not be representative enough for the data distribution as a whole. Alternatively, diversity-based criteria have the advantage of selecting a set of most representative samples, related to the labeled ones, from those in the rest of the unlabeled set. The intuition is that there is no need to repeatedly annotate those samples with context information if the most representative one has already been covered. Mutual information, Fisher information, K-centers and core sets, calculated among either model predictions or image features, are often used to ensure the diversity. Although alleviating redundancy and outliers, a serious hurdle of diversity-based criteria is the computational complexity for a large pool of unlabeled samples. This issue was addressed by measuring diversity over patches augmented from the same sample, making the calculation much more manageable. To exploit the benefits and potentials of the two selecting aspects, as well as the described ACFT methodology, consider the mixture strategy of combing uncertainty and diversity explicitly. Prior techniques further compute the selection criteria from an ensemble of CNNs—these approaches are, however, very costly in computation, as they must train a set of models to compute their uncertainty measure based on models' disagreements. Prior known methods are fundamentally different from the described ACFT methodology in that they all repeatedly retrained CNNs from scratch at each step, whereas ACFT methodology continually fine-tune the (fine-tuned) CNN incrementally. As a result, the ACFT methodology offers several advantages as listed in the introduction, and leads to dramatic annotation cost reduction and computation efficiency. Besides, through experiments, it was found that there are only seven fundamental patterns in CNN predictions (refer to the section entitled "Illustrating active candidate selection"). Multiple methods may be developed to select a particular pattern: entropy, Gaussian distance, and standard deviation would seek Pattern A, while diversity, variance, and divergence look for Pattern C. The results provided here are first to analyze the prediction patterns in active learning and investigate the effectiveness of typical patterns rather than comparing the many methods.

FIG. 1F depicts Table 1 at element 199, for implementing Active Continual Fine-Tuning ("ACFT"), in accordance with described embodiments. Specifically shown are active selection patterns analysis. The data shown here illustrates the relationships among seven prediction patterns and four active selection criteria, assuming that a candidate $C_i$ has eleven (11) augmented patches, and their probabilities $P_i$ are predicted by the current CNN, presented in the second column. With majority selection, the entropy and diversity are calculated based on the top 25% (three (3) patches in this illustration) highest confidences on the dominant predicted category. The first choice of each method (column) is bolded and the second choice is underlined.

Proposed Method:

ACFT was conceived in the context of computer-aided diagnosis (CAD) applied to medical imaging. A CAD system typically employs a candidate generator, which can quickly produce a set of candidates, among which some are true positives and others are false positives. To train a classifier, each of the candidates must be labeled. In this work, an object to be labeled is considered as a "candidate" in general. The method assumes that each candidate takes one of $|y|$ possible labels. To boost CNN performance for CAD systems, multiple patches are usually generated automatically for each candidate through data augmentation; those patches that are generated from the same candidate inherit the candidate's label. In other words, all labels are acquired at the candidate level. Mathematically, given a set of candidates, $u=\{C_1, C_2, \ldots C_n\}$, where n is the number of candidates, and each candidate $C_i=\{x_i^1, x_i^2, \ldots x_i^m\}$ is associated with m patches, the ACFT algorithm iteratively selects a set of candidates for labeling as illustrated in Algorithm 1 (FIG. 1E, element 195).

ACFT is generic and applicable to many tasks in computer vision and image analysis. For clarity, the ideas behind ACFT were illustrated with the PLACES-3 dataset for scene classification in natural images (refer also to FIG. 10), where no candidate generator is needed, as each image may be directly regarded as a candidate. Designing an active learning algorithm involves two key issues: (1) how to determine the "worthiness" of a candidate for annotation and (2) how to update the classifier/learner. In the following sections, a hypothesis is first set forth (refer to the section entitled "Illustrating active candidate selection" with reference to FIG. 2A and Table 1 at FIG. 1E), and then each of the components for the active selection criteria are detailed along with corresponding rationale and benefit.

Figure 2A:
FIG. 2A depicts how automatic data augmentation inevitably generates noisy patches, and as such, there is no need to classify all patches confidently.

FIG. 2A depicts how automatic data augmentation inevitably generates noisy patches, and as such, there is no need to classify all patches confidently.

Therefore, a majority selection is proposed, which computes active selection criteria on only the top 25% of the patches with the highest confidences on the dominant predicted category. To demonstrate the necessity of majority selection, two images were illustrated (A and B) and their augmented patches, arranged according to the dominant category predicted by the CNN. Based on Places-3, Image A is labeled as living room, and its augmented patches are mostly incorrectly classified by the current CNN; therefore, including it in the training set is of great value. On the contrary, Image B is labeled as office, and the current CNN classifies most of its augmented patches as office with high confidence; labeling it would be of limited utility. Without majority selection, the criteria would mislead the selection, as it indicates that Image B is more diverse than Image A (297.52 vs. 262.39) while sharing similar entropy (17.33 vs. 18.50). With majority selection, the criteria show that Image A is considerably more uncertain and diverse than Image B, measured by either entropy (4.59 vs. 2.17) or diversity (9.32 vs. 0.35), and as expected, more worthy of labeling. From this active selection analysis, the majority selection is considered a critical component in the described ACFT methodology.

Illustrating Active Candidate Selection:

Depicted here at FIG. 2A, the active candidate selection process is depicted for multi-class classification. To facilitate comprehension, refer to the data set forth at Table 1 (FIG. 1E, element 195) which illustrates the process in the context of binary classification. Assuming the prediction of patch $x_i^j$ by the current CNN is $P_i^j$, the histogram of $P_i^j$, $j \in [1,m]$ may thus be called the prediction pattern of candidate $C_i$. As shown in Row 1 of Table 1, in binary classification, there are seven typical prediction patterns:

1. Pattern A is mostly concentrated at 0.5, with a higher degree of uncertainty. Most active learning algorithms favor these types of candidates as they are effective for reducing uncertainty.
2. Pattern B is flatter than Pattern A, as the patches' predictions are spread widely from 0 to 1 with a higher degree of inconsistency among the patches' predictions. Since all the patches belonging to a candidate are generated via data augmentation, they (at least the majority) are expected to make similar predictions. These types of candidates have the potential to significantly enhance the current CNN's performance.
3. Pattern C is clustered at both ends, with a higher degree of diversity. These types of candidates are most likely associated with noisy labels at the patch level as illustrated in FIG. 2(c), and they are the least favorable for use in active selection because they may cause confusion when fine-tuning the CNN.
4. Patterns D and E are clustered at either end (i.e., 0 or 1), with a higher degree of certainty. These types of candidates should not undergo annotation at this step because it is likely the current CNN has correctly predicted them, and therefore these candidates would contribute very little towards fine-tuning the current CNN.

5. Patterns F and G have a higher degree of certainty for some of the patches' predictions but are associated with some outliers. These types of candidates are valuable because they are capable of smoothly improving the CNN's performance. While such candidates might not make dramatic contributions, they do not significantly degrade the CNN's performance either.

Seeking worthy candidates: In active learning, the key is to develop criteria for determining candidate annotation "worthiness". As utilized here, the criteria for candidate "worthiness" are based on a simple, yet powerful, observation: all patches augmented from the same candidate (FIG. 2A) share the same label; therefore, they are expected to have similar predictions by the current CNN. As a result, their entropy and diversity provide a useful indicator of the "power" of a candidate for elevating the performance of the current CNN. Intuitively, entropy captures classification certainty—a higher uncertainty value denotes a greater degree of information (e.g., pattern A in Table 1), whereas diversity indicates prediction consistency among the candidate patches—a higher diversity value denotes a greater degree of prediction inconsistency (e.g., pattern C in Table 1). Formally, assuming that each candidate takes one of $|\gamma|$ possible labels, the entropy and diversity of $C_i$ is defined at equation 1, as follows:

$$e_i = -\frac{1}{m}\sum_{k=1}^{|\gamma|}\sum_{j=1}^{m} P_i^{j,k} \log P_i^{j,k},$$

$$d_i = \sum_{k=1}^{|\gamma|}\sum_{j=1}^{m}\sum_{l=j}^{m} (P_i^{j,k} - P_i^{l,k}) \log \frac{P_i^{j,k}}{P_i^{l,k}}$$

and combining entropy and diversity yields as is defined at equation 2, as follows:

$$a_i = \lambda_1 e_i + \lambda_2 d_i$$

where $\lambda_1$ and $\lambda_2$ are trade-offs between entropy and diversity. The method uses two parameters for convenience, to easily turn on/off entropy or diversity during experiments. Refer also to Equations 1 and 2 as set forth at FIG. 2B, elements 205 and 206, respectively.

Figure 3A:
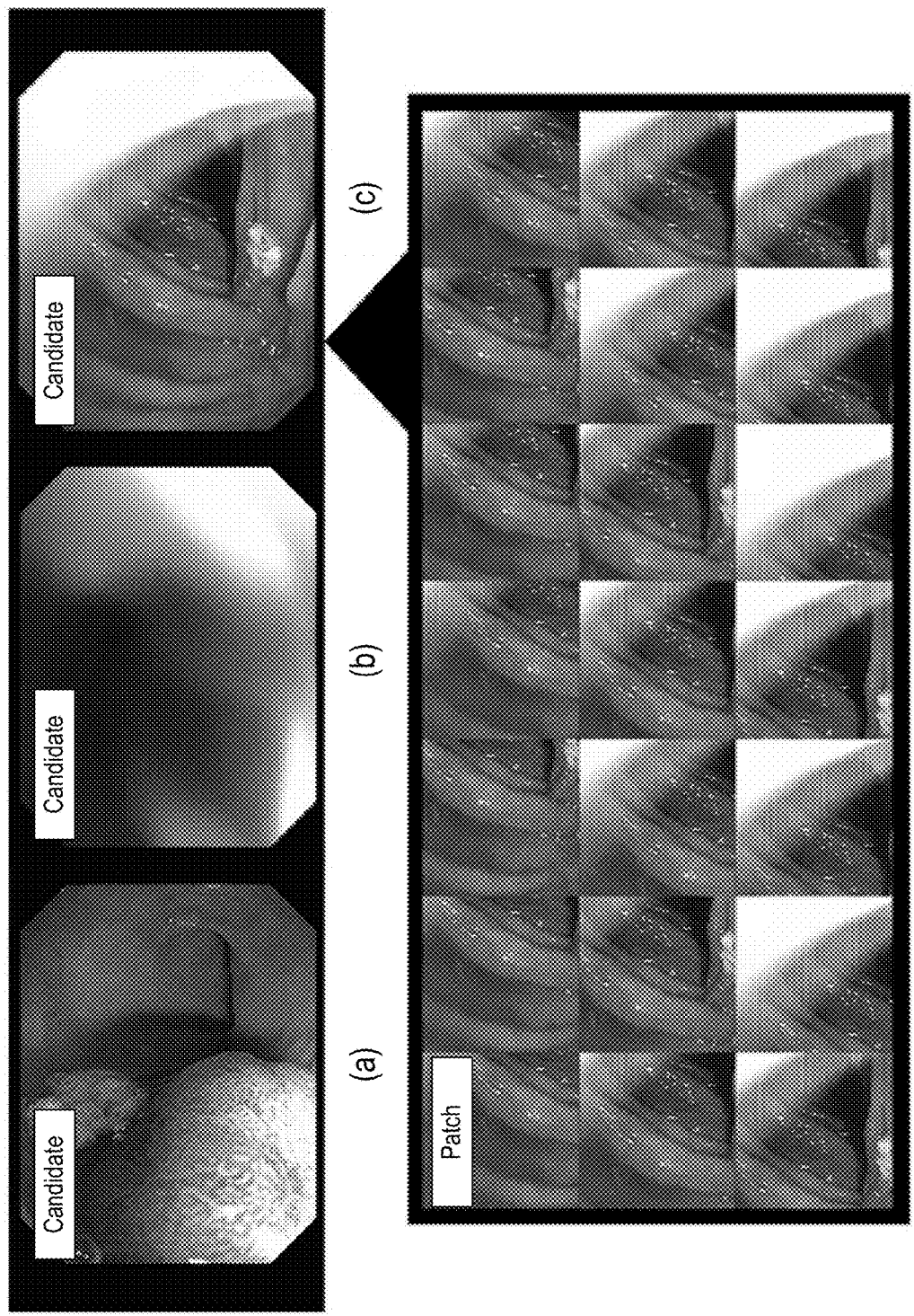
FIG. 3A depicts three (3) examples of colonoscopy frames.

FIG. 3A depicts three (3) examples of colonoscopy frames, including: (a) informative, (b) non-informative, and (c) ambiguous. "Ambiguous" frames are labeled as "informative" because experts label frames based on the overall quality: if over 75% of a frame (i.e., candidate in this application) is clear, the frame is considered "informative". As a result, an ambiguous candidate contains both clear and blurred components, and generates noisy labels at the patch level from automatic data augmentation. For example, the entire frame (c) is labeled as "informative," but not all the patches (d) associated with this frame are "informative", although they inherit the "informative" label. This limitation is the main motivation for the majority selection approach in the described ACFT method.

Handling noisy labels via majority selection: Automatic data augmentation is essential for boosting CNN performance, but it inevitably generates "hard" samples for some candidates, as shown in FIG. 2(c), injecting noisy labels. Therefore, to significantly enhance the robustness of the described ACFT methodology, entropy and diversity were computed by selecting only a portion of the patches of each candidate according to the predictions by the current CNN. Specifically, for each candidate $C_i$, its dominant category is first determined, which is defined by the category with the highest confidence in the mean prediction, as defined by equation 3, as follows:

$$\hat{y}_i = \operatorname*{argmax}_{y \in \mathcal{Y}} \frac{1}{m}\sum_{j=1}^{m} P_i^{j,y}$$

where $P_i^{j,y}$ is the output of each patch j from the current CNN given $\forall x^i \in C_i$ on label y. Refer also to Equation 3 as set forth at FIG. 2B, element 207. After sorting $P_i$ according to dominant category $\hat{y}_i$, equation 2 is then applied to the top $\alpha \times 100\%$ of the patches to construct the score matrix $a_i$ of size $\alpha m \times \alpha m$ for each candidate $C_i$ in u. The proposed majority selection method automatically excludes the patches with noisy labels (refer again to Table 1: diversity and diversity $\alpha$) because of their low confidences.

Figure 3B:
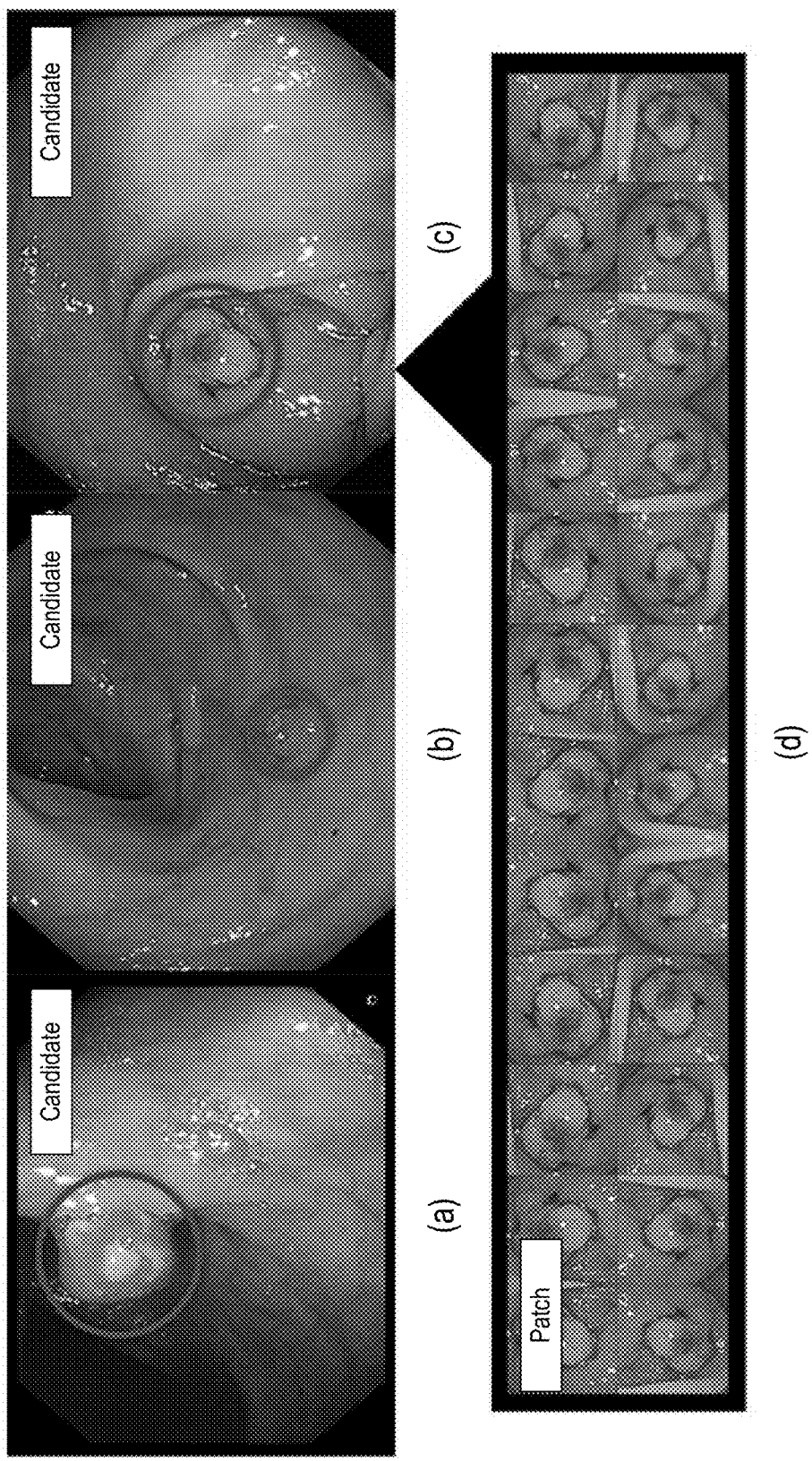
FIG. 3B depicts polyps in colonoscopy videos with different shape and appearance.

FIG. 3B depicts polyps in colonoscopy videos with different shape and appearance.

Figure 4A:
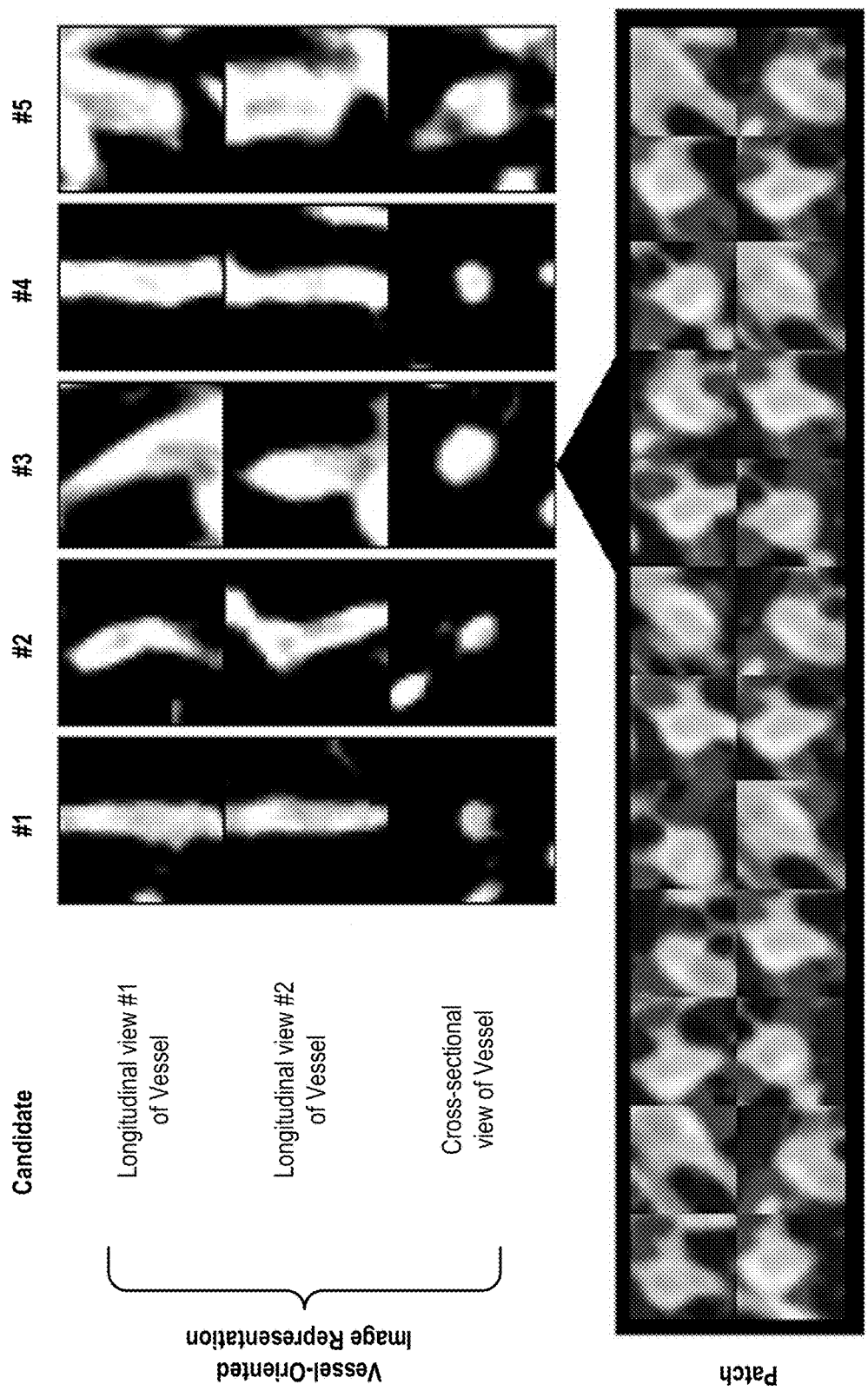
FIG. 4A depicts five different pulmonary embolism candidates in the vessel-oriented image representation.

FIG. 4A depicts five different pulmonary embolism candidates in the vessel-oriented image representation. It was adopted in this work because it achieves great classification accuracy and accelerates CNN training convergence.

Injecting randomization in active selection: With other techniques, simple random selection may outperform active selection at the beginning, because the active selection method depends on the current CNN selecting examples for labeling. As a result, a poor selection made at an early stage may adversely affect the quality of subsequent selections, whereas the random selection approach is less frequently locked into a poor hypothesis. In other words, the active selection method concentrates on exploiting the knowledge gained from the labels already acquired to further explore the decision boundary, whereas the random selection approach concentrates solely on exploration, and is thereby able to locate areas of the feature space where the classifier performs poorly. Therefore, an effective active learning strategy must strike a balance between exploration and exploitation. Towards this end, randomization is injected into the described method by selecting actively according to the sampling probability $a_i^s$, according to equation 4, as follows:

$$a_i' = (a_i' - a_{\omega b}')/(a_1' - a_{\omega b}'),$$

$$a_i^s = a_i'/\sum_i a_i', \forall i \in [1, \omega b]$$

where $a_i'$ is sorted $a_i$ according to its value in descending order, and $\omega$ is named random extension. Refer also to Equation 4 as set forth at FIG. 4B, element 407. Suppose b number of candidates are required for annotation. Instead of selecting top b candidates, the method extends the candidate selection pool to $\omega b$. Candidates are then selected from this pool with their sampling probabilities $a_i^s$ to inject randomization.

Experiments

Medical Applications:
Colonoscopy Frame Classification: Image quality assessment in colonoscopy can be viewed as an image classification task whereby an input image is labeled as either informative or non-informative. One way to measure the quality of a colonoscopy procedure is to monitor the quality of the captured images. Such quality assessment can be used during live procedures to limit low-quality examinations or, in a post-processing setting, for quality monitoring purposes. In this application, colonoscopy frames are regarded as candidates, since the labels (informative or non-informative) are associated with frames as illustrated in FIG. 3A (sub-elements a-c). In total, there are 4,000 colonoscopy candidates from six (6) complete colonoscopy videos. A trained expert then manually labeled the collected images as informative or non-informative (refer again to line 11 in Algorithm 1 as set forth at FIG. 1E). A gastroenterologist further reviewed the labeled images for corrections. The labeled frames are separated at the video level into training and test sets, each containing approximately 2,000 colonoscopy frames. For data augmentation, 21 patches were extracted from each frame as shown in FIG. 3A (sub-element d).

Polyp Detection: Polyps, as shown in FIG. 3B, can present themselves in the colonoscopy with substantial variations in color, shape, and size. The variable appearance of polyps can often lead to misdetection, particularly during long and back-to-back colonoscopy procedures where fatigue negatively affects the performance of colonoscopies. Computer-aided polyp detection may enhance optical colonoscopy screening accuracy by reducing polyp misdetection. In this application, each polyp detection is regarded as a candidate. The dataset contains 38 patients with one video each. The training dataset is composed of 21 videos (11 with polyps and 10 without polyps), while the testing dataset is composed of 17 videos (8 videos with polyps and 9 videos without polyps). At the video level, the candidates are divided into the training dataset (16,300 candidates) and test dataset (11,950 candidates). At each polyp candidate location with the given bounding box, data augmentation was performed by a factor f∈{1.0, 1.2, 1.5}. At each scale, patches were extracted after the candidate is translated by 10 percent of the resized bounding box in vertical and horizontal directions. Each resulting patch was further rotated eight (8) times by mirroring and flipping. The patches generated by data augmentation belong to the same candidate. Each candidate contains 24 patches.

Pulmonary Embolism Detection: Pulmonary embolism (PE) is a major national health problem, and computer-aided PE detection could play a major role in improving PE diagnosis and decreasing the reading time required for CTPA datasets. A database consisting of 121 CTPA datasets with a total of 326 PE instances was employed. Each PE detection is regarded as a candidate with 50 patches. The candidates were divided at the patient level into a training dataset, with 434 true positives (199 unique PE instances) and 3,406 false positives, and a testing dataset, with 253 true positives (127 unique PE instances) and 2,162 false positives. The overall PE probability was calculated by averaging the probabilistic prediction generated for the patches within a given PE candidate after data augmentation.

Baselines and Implementation

Active learning strategy baselines: Prior techniques reported the state-of-the-art performance of fine-tuning and learning from scratch using entire datasets, which are used to establish baseline performance for comparison. While others investigated the performance of (partial) fine-tuning using a sequence of partial training datasets, the dataset partitions utilized for the described methodology and complementary experiments are nevertheless different from the dataset partitions utilized by others. Therefore, to ensure a fair comparison earlier techniques, RFT was introduced, which fine-tunes the original CNN model $M_0$ from the beginning, using all available labeled samples $L \cup Q$ where Q is randomly selected at each step.

FIG. 4C depicts Table 2 at element 495, depicting an active learning strategy definition. Specifically, different learning strategies are codified covering the makeup of training samples and the initial CNN weights of fine-tuning.

FIG. 4D depicts Table 3 at element 496, listing the earning parameters used for training and fine-tuning of AlexNet for AFT in the described experiments. The term $\mu$ is the momentum, $lr_{fc8}$ is the learning rate of the weights in the last layer, $\alpha$ is the learning rate of the weights in the rest layers, and $\gamma$ determines how lr decreases over epochs. "Epochs" indicates the number of epochs used in each step. For ACFT, all the parameters are set to the same as AFT except the learning rate lr, which is set to $\frac{1}{10}$ of that for AFT.

Several active learning strategies are summarized in Table 2. Studying different active learning strategies is important because active learning procedure can be very computationally inefficient in practice, in terms of label reuse and model reuse. Two strategies are presented that aim at overcoming the above limitations. First, it is proposed to combine newly annotated data with the labeled data that is misclassified by the current CNN. Second, continual fine-tuning is proposed to speed up model training and, in turn, encourage data reuse. $ACFT_{(HQ)}$ denotes the optimized learning strategy, which continually fine-tunes the current CNN model $M_{t-1}$ using newly annotated candidates enlarged by those misclassified candidates; that is, $Q \cup H$. Compared with other learning strategy baselines as codified in Table 2, $ACFT_{(HQ)}$ saves training time through faster convergence compared with repeatedly fine-tuning the original pre-trained CNN, and boosts performance by eliminating easy samples, focusing on hard samples, and preventing catastrophic forgetting. In all three applications, the ACFT begins with an empty training dataset and directly uses pre-trained CNNs (AlexNet and GoogLeNet) on ImageNet.

Figure 5A:
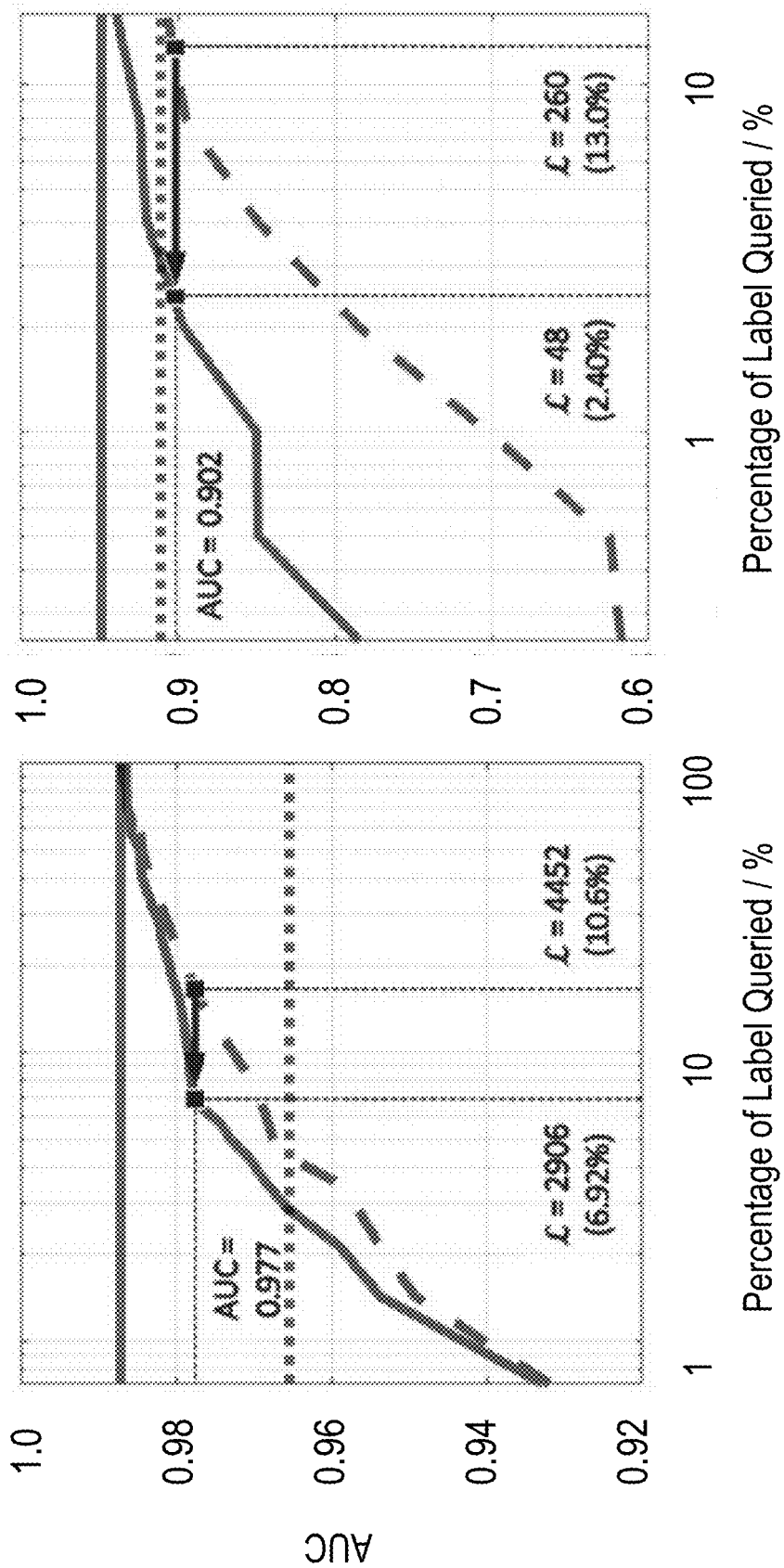
FIGS. 5A and 5B depict how the ACFT methodology minimizes the number of samples for experts to label by iteratively recommending the most informative and representative samples.
Figure 5B:
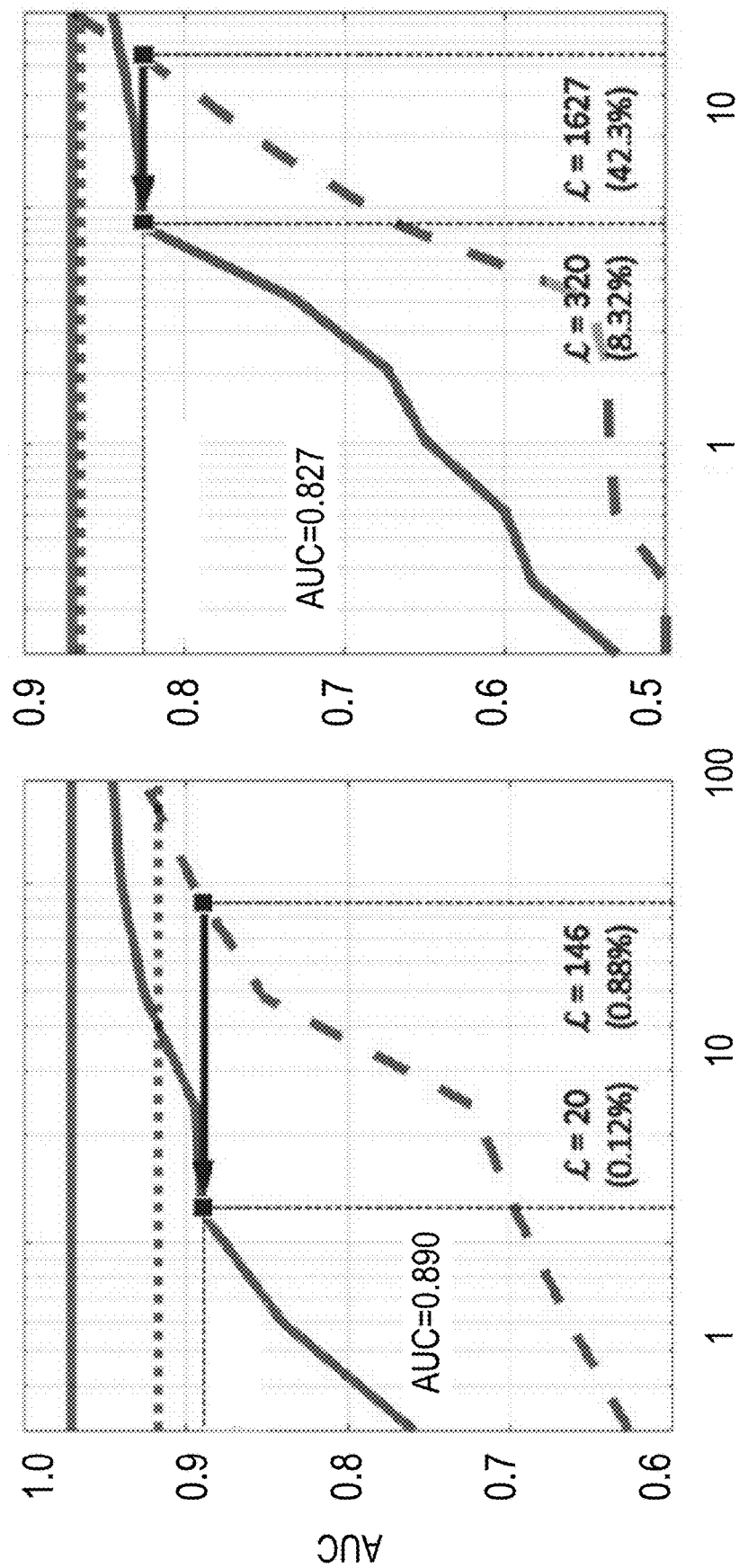

FIGS. 5A and 5B depict how the ACFT methodology minimizes the number of samples for experts to label by iteratively recommending the most informative and representative samples. For scene classification (a), by actively selecting 2,906 images (6.92% of the entire dataset), ACFT (solid block) offers equivalent performance to the use of 4,452 images through random selection, thus saving 34.7% annotation cost relative to random fine-tuning (RFT in dashed orange). Furthermore, with 1,176 actively-selected images (2.80% of the whole dataset), ACFT achieves performance equivalent to full training (dashed black) using 42,000 images, thereby saving 97.2% annotation cost (relative to full training). In sub-elements (b)-(d) of FIGS. 5A and 5B, the major results are highlighted that, compared with RFT, reduce the cost of annotation through the use of ACFT by 81.5% for colonoscopy frame classification, 86.3% for polyp detection, and 80.3% for pulmonary embolism detection. Following the standard active learning experimental setup, both ACFT and RFT select samples from the remaining training dataset; they will eventually use the same whole training dataset, naturally yielding similar performance at the end. However, the goal of active learning is to find such sweet spots where a learner can achieve an acceptable performance using the least number of labeled samples.

Figure 6A:
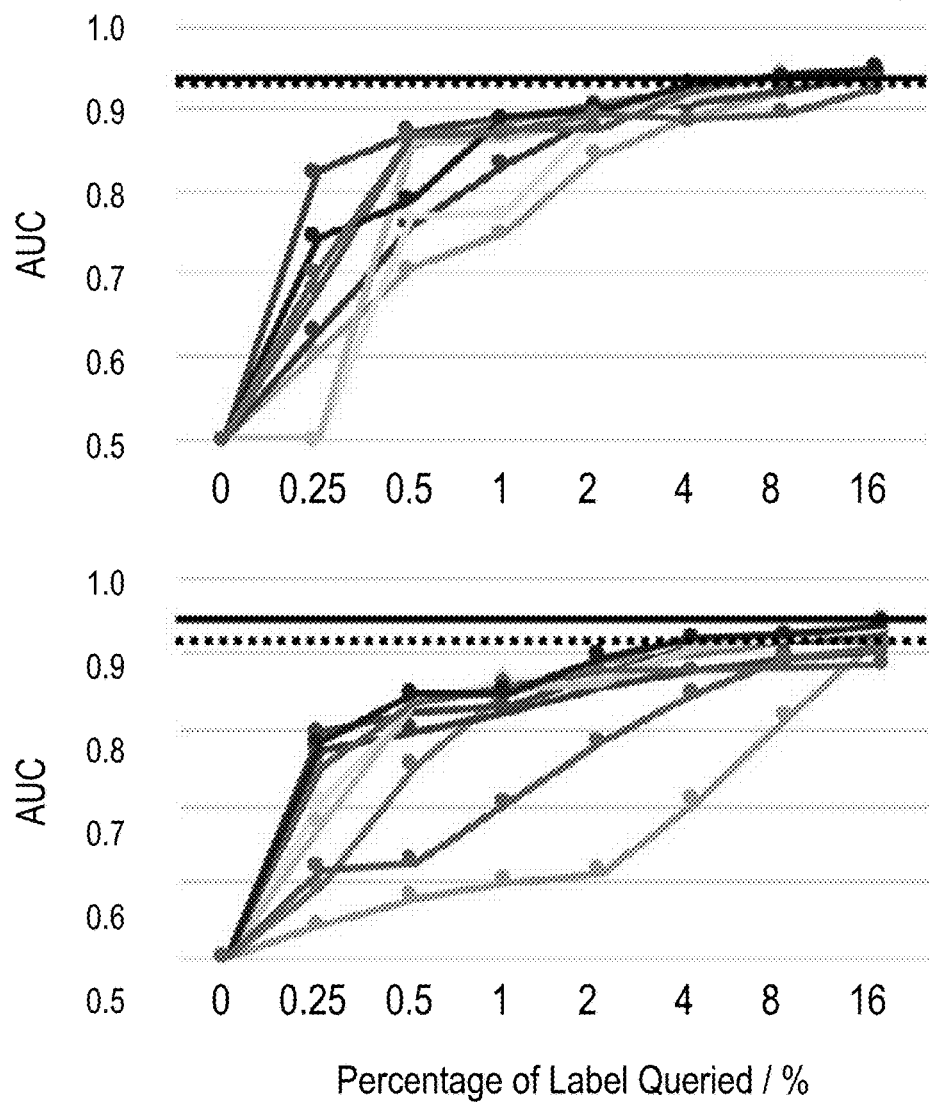
FIGS. 6A, 6B, and 6C compare eight active selection approaches with random selection on AlexNet (top panel) and GoogLeNet (bottom panel) for three distinct medical applications.
Figure 6B:
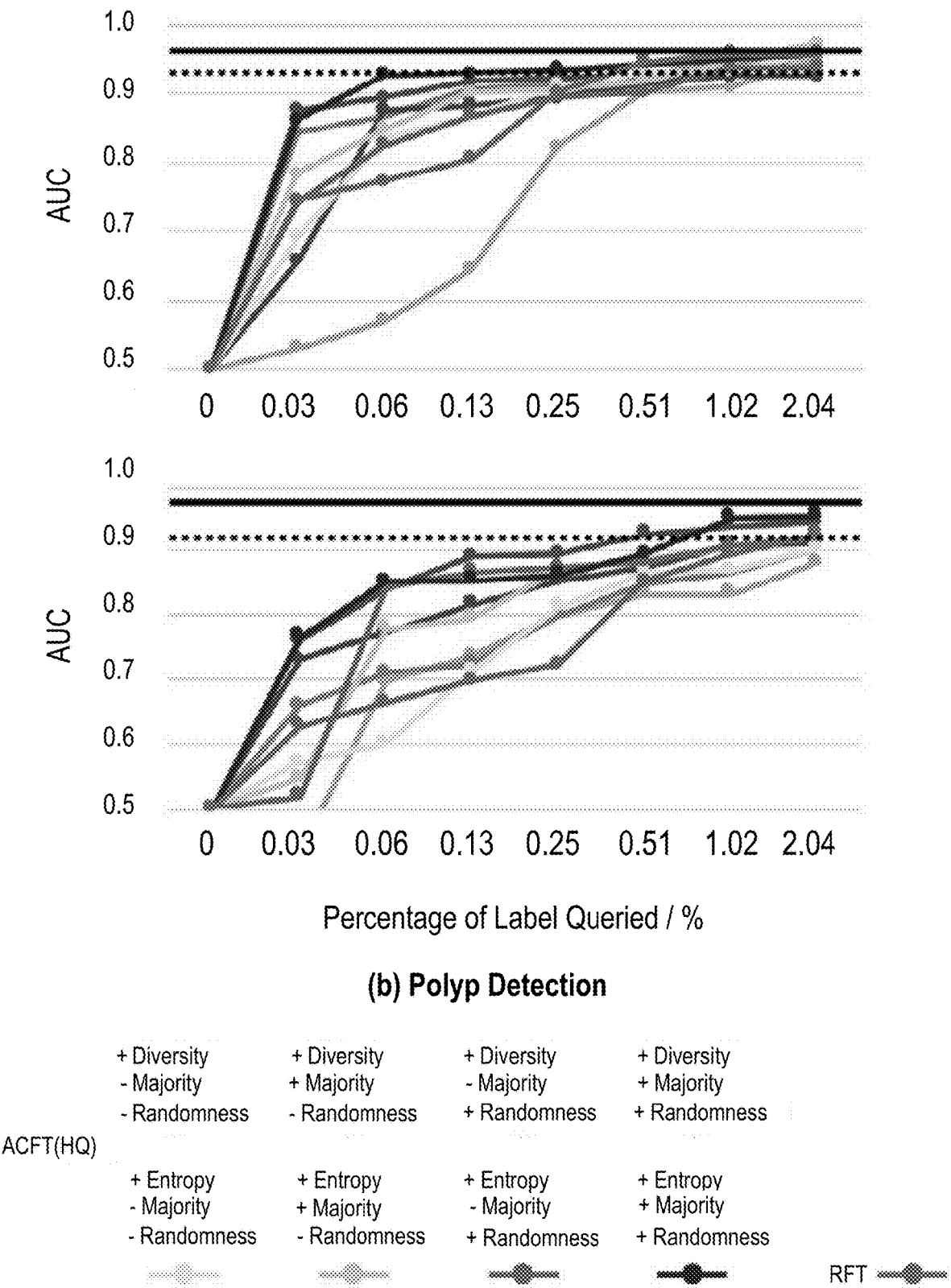
Figure 6C:
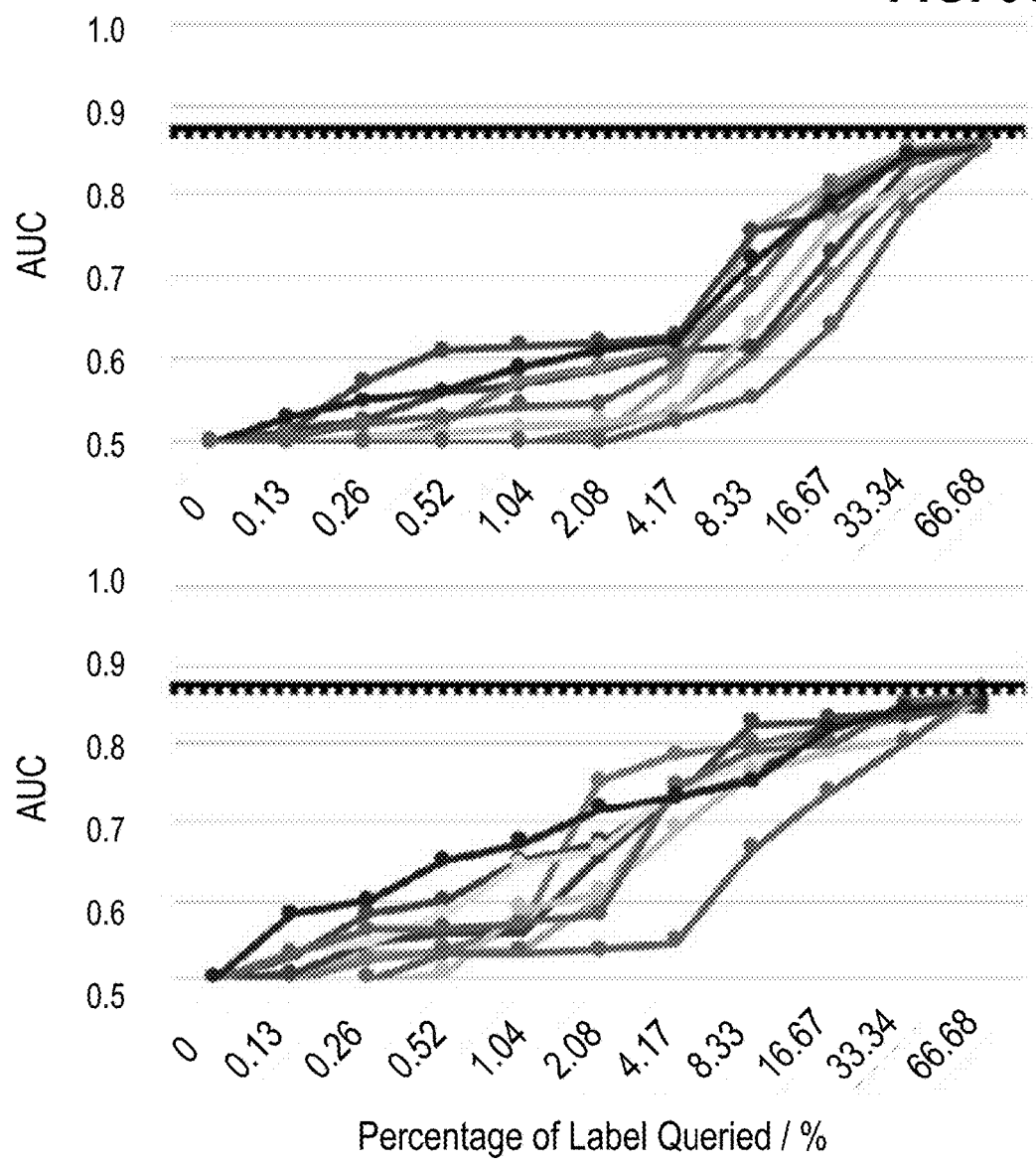

FIGS. 6A, 6B, and 6C compare eight active selection approaches with random selection on AlexNet (top panel) and GoogLeNet (bottom panel) for three distinct medical applications, including (a) colonoscopy frame classification, (b) polyp detection, and (c) pulmonary embolism detection, demonstrating consistent patterns with AlexNet. The solid black line denotes the current state-of-the-art performance of fine-tuning using full training data and the dashed black line denotes the performance of training from scratch using full training data.

Figure 7A:
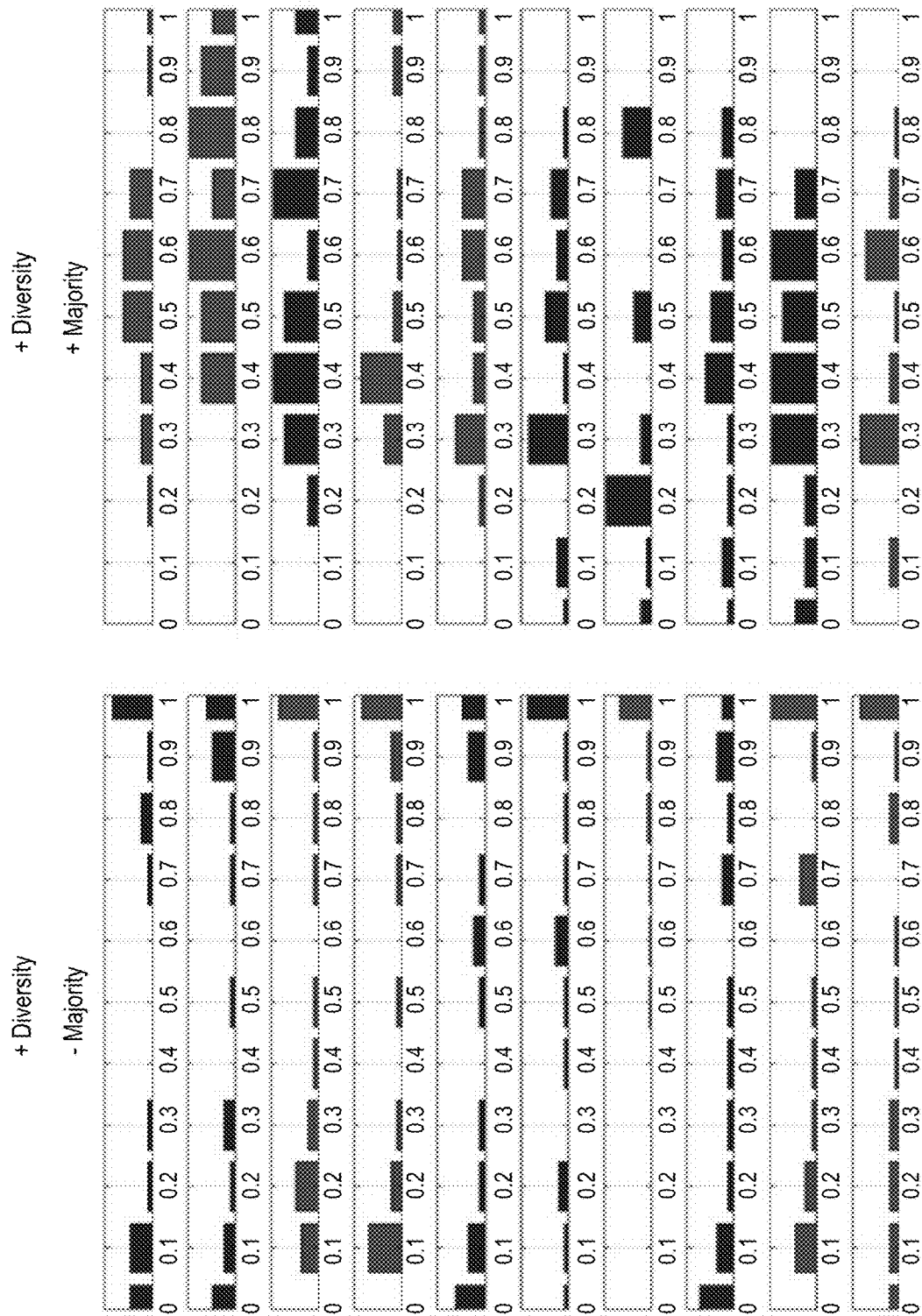
FIGS. 7A and 7B show a distribution of predictions for the top ten candidates actively selected by the four ACFT methods at Step 3 in colonoscopy frame classification.
Figure 7B:
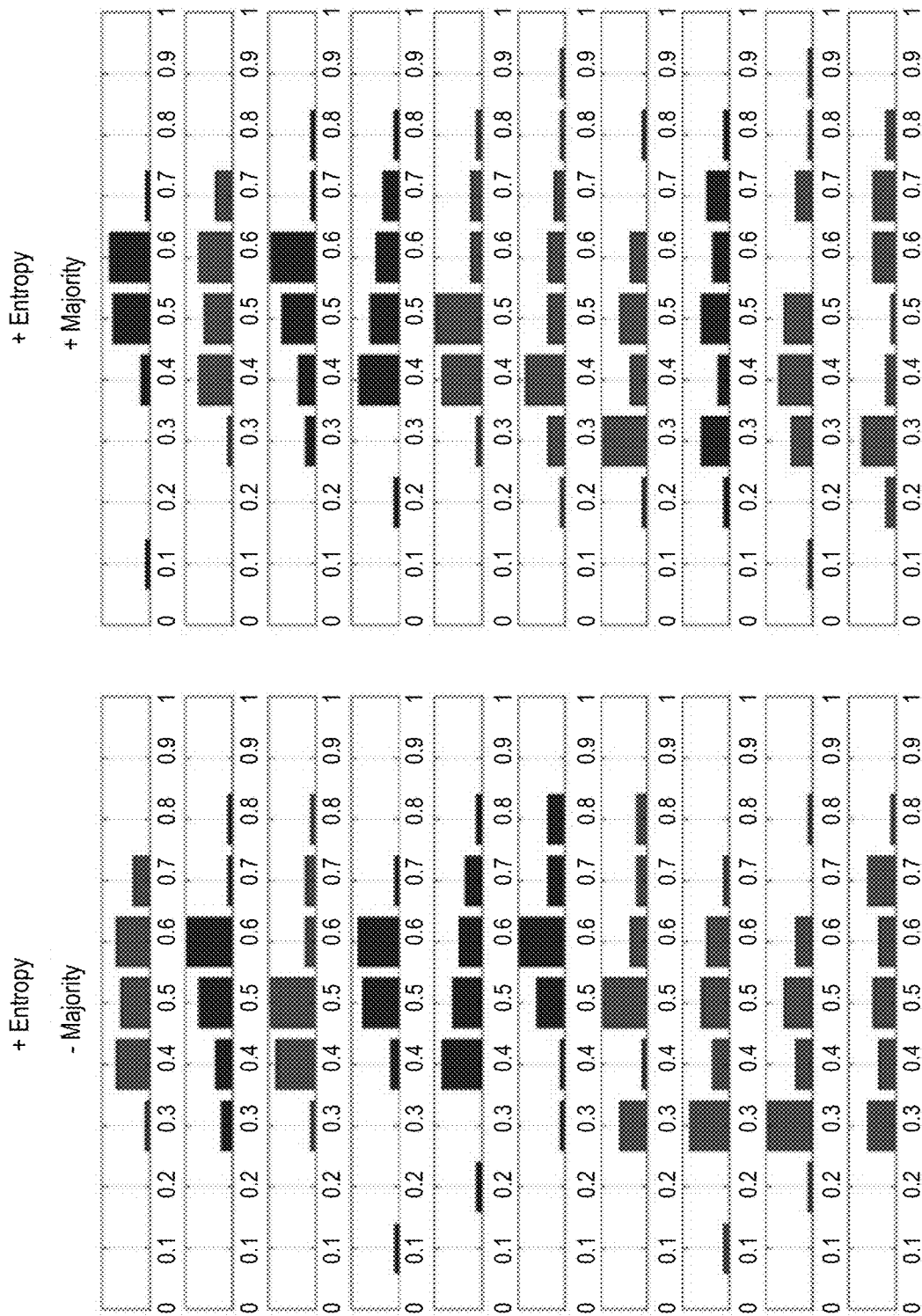

FIGS. 7A and 7B show a distribution of predictions for the top ten candidates actively selected by the four ACFT methods at Step 3 in colonoscopy frame classification. Positive candidates are shown in black and negative candidates are shown in dark gray. This visualization confirms the assumption in Table 1 that diversity+majority selection criteria prefers Pattern B whereas diversity suggests Pattern C; both entropy and entropy+majority favor Pattern A due to its higher degree of uncertainty. However, in this case at Step 3, with entropy+majority selection criteria, there are no more candidates with Pattern A; therefore, candidates with Pattern B are selected.

FIG. 7C depicts Table 4 at element 798, providing a comparison of proposed active learning strategies and selection criteria. As measured by the Area under the Learning Curve (ALC), bolded values in the table indicate the outstanding learning strategies (see Table 2 at FIG. 4C) using certain active selection criteria, and starred values represent the best performance taking both learning strategies and active selection criteria into consideration. For all three applications, baseline performance of random fine-tuning (RFT) is reported using AlexNet in the table footnote. Considering the variance of random sampling for each active learning step, five independent trials were conducted for RFT and report the mean and standard deviation (mean±s.d.).

Experimental settings: Experiments investigated the effectiveness of ACFT in four (4) applications: scene classification, colonoscopy frame classification, polyp detection, and pulmonary embolism (PE) detection. Ablation studies have been conducted to confirm the significant design of the majority selection and randomization, built upon conventional entropy and diversity based active selection criteria. For all four applications, α was set to ¼ and ω was set to 5. The deep learning library Matlab and Caffe were utilized to implement active learning and transfer learning. The experiments were built upon AlexNet and GoogLeNet because their architectures offer an optimal depth balance, deep enough to investigate the impact of ACFT and AFT on pre-trained CNN performance, but shallow enough to conduct experiments quickly. The learning parameters used for training and fine-tuning of AlexNet in the experiments are summarized in Table 3 (refer again to FIG. 4D). The Adam optimizer is utilized to optimize the objective functions described by this paper. The batch size is 512 in the learning procedure.

Results:

As depicted at FIGS. 5A and 5B an overall performance gain is depicted between the active continual fine-tuning (ACFT) and random fine-tuning (RFT), revealing the amount of annotation effort that has been reduced in each application. FIGS. 6A, 6B, and 6C compare eight (8) different active selection criteria, demonstrating that majority selection and randomness are critical in finding the most representative samples to elevate the current CNN's performance. FIGS. 7A and 7B further present the observed distribution from each active selection criteria, qualitatively confirming the rationale of the devised candidate selecting approaches. Table 4 (see FIG. 7C) then compares four different active learning strategies, suggesting that continual fine-tuning using newly annotated candidates enlarged by those misclassified candidates significantly saves computational resources while maintaining the compelling performance in all three medical applications.

ACFT reduces 35% annotation effort in scene classification: As depicted at FIG. 5A (sub-element a), a comparison is provided between ACFT and RFT in scene classification using the PLACES-3 dataset. For RFT, six (6) different sequences are generated via systematic random sampling. The final curve is plotted showing the average performance of six runs. As shown in FIG. 5A (sub-element a), ACFT, with only 2,906 candidate queries, can achieve performance equivalent to RFT with 4,452 candidate queries, as measured by the Area Under the Curve (AUC); moreover, using only 1,176 candidate queries, ACFT can achieve performance equivalent to full training using all 42,000 candidates. Therefore, 34.7% of the RFT labeling costs and 97.2% of the full training costs could be saved using ACFT. When nearly 100% training data are used, the performance continues to improve, suggesting that the dataset size is still insufficient, given 22 layers GoogLeNet architecture. ACFT is a general algorithm that is not only useful for medical datasets but other datasets as well, and is also effective for multi-class problems.

ACFT reduces 82% annotation effort in colonoscopy frame classification: As depicted at FIG. 5A (sub-element b), ACFT with approximately 120 candidate queries (6%), achieves performance equivalent to a 100% trained dataset fine-tuned from AlexNet (solid black line, AUC=0.9366), and, with only 80 candidate queries (4%), can achieve performance equivalent to a 100% training dataset learned from scratch (dashed black line, AUC=0.9204). Using only 48 candidate queries, ACFT equals the performance of RFT at 260 candidate queries. Therefore, about 81.5% of the labeling cost associated with RFT in colonoscopy frame classification is recovered using ACFT. Detailed analysis in FIGS. 6A, 6B, and 6C reveals that during the early stages, RFT yields performance superior to some of the active selecting processes because: 1) random selection gives samples with the positive-negative ratio compatible with the testing and validation dataset; 2) the pre-trained CNN gives poor predictions in the domain of medical imaging, as it was trained by natural images. Its output probabilities are mostly inconclusive or even opposite, yielding poor selection scores. However, with randomness injected (refer to the section entitled "Injecting randomization in active selection"), ACFT (+majority and +randomness) shows superior performance, even at early stages, with continued performance improvement during subsequent steps. Besides, evidenced by Table 4 (see FIG. 7C), ACFT performs comparably with AFT, but, unlike the latter, does not require use of the entire labeled dataset or fine-tuning from the beginning.

ACFT reduces 86% annotation effort in polyp detection: As depicted at FIG. 5B (sub-element c), ACFT with approximately 320 candidate queries (2.04%), can achieve performance equivalent to a 100% training dataset fine-tuned from AlexNet (solid black line, AUC=0.9615), and, with only 10 candidate queries (0.06%), can achieve performance equivalent to a 100% training dataset learned from scratch (dashed black line, AUC=0.9358). Furthermore, ACFT, using only 20 candidate queries, achieves performance equivalent to RFT using 146 candidate queries. Therefore, nearly 86.3% of the labeling cost associated with the use of RFT for polyp detection could be recovered with the described ACFT methodology. The fast convergence and outstanding performance of ACFT is attributable to the majority selection and randomization method, which can both efficiently select the informative and representative candidates while excluding those with noisy labels, yet still boost the performance during the early stages. For example, the diversity criteria, if without using majority selection, would strongly favor candidates whose prediction pattern resembles Pattern C (see Table 1 at FIG. 1E), thus performing poorer than RFT due to noisy labels generated through data augmentation.

ACFT reduces 80% annotation effort in pulmonary embolism detection: As depicted at FIG. 5B (sub-element d), ACFT with 2,560 candidate queries (66.68%) nearly achieves performance equivalent to both the 100% training dataset fine-tuned from AlexNet and learning from scratch (solid black line and dashed black line, where AUC=0.8763 and AUC=0.8706, respectively). With 320 candidate queries, ACFT can achieve the performance equivalent to RFT using 1,627 candidate queries. Based on this analysis, the cost of annotation in pulmonary embolism detection can be reduced by 80.3% using ACFT compared with RFT.

Observations on active selection criteria: Throughout the experiments, the active selection process was meticulously monitored and examined the selected candidates then examined. For example, the top ten candidates included were selected by the four ACFT methods at Step 3 in colonoscopy frame classification in FIGS. 7A and 7B. From this process, the following may thus be observed:

Patterns A and B are dominant in the earlier stages of ACFT as the CNN has not been fine-tuned properly to the target domain;

Patterns C, D and E are dominant in the later stages of ACFT as the CNN has been largely fine-tuned on the target dataset;

Majority selection is effective for excluding Patterns C, D, and E, whereas entropy only (without the majority selection) can handle Patterns C, D, and E reasonably well;

Patterns B, F, and G generally make good contributions to elevating the current CNN's performance;

Entropy and entropy+majority favor Pattern A due to its higher degree of uncertainty; and Diversity+majority prefers Pattern B whereas diversity prefers Pattern C. This is why diversity may cause sudden disturbances in the CNN's performance and why diversity+majority is generally preferred.

Comparison of proposed learning strategies: As summarized in Table 2 at FIG. 4C, several active learning strategies can be derived. The prediction performance was evaluated according to the Area under the Learning Curve (ALC), in which the learning curve plots AUC as a function of the number of labels queried was computed on the testing dataset. Table 4 at FIG. 7C shows the ALC of $ACFT_{(Q)}$, $ACFT_{(LQ)}$, $AFT_{(LQ)}$ and $ACFT_{(HQ)}$, compared with RFT. These comprehensive experiments have therefore demonstrated that:

1. $ACFT_{(Q)}$ considers only newly selected candidates for fine-tuning, resulting in an unstable CNN performance due to the catastrophic forgetting of the previous samples;
2. $ACFT_{(LQ)}$ requires a careful parameter adjustment. Although its performance is acceptable, it requires the same computing time as $AFT_{(LQ)}$, indicating that there is no advantage to continually fine-tuning the current CNN;
3. $AFT_{(LQ)}$ shows the most reliable performance compared with $ACFT_{(Q)}$ and $ACFT_{(LQ)}$; and
4. The optimized version, $ACFT_{(HQ)}$ shows comparable performance to $AFT_{(LQ)}$ and occasionally outperforms $AFT_{(LQ)}$ by eliminating easy samples, focusing on hard samples, and preventing catastrophic forgetting.

In summary, the experimental results suggest that (1) it is unnecessary to retrain models repeatedly from scratch for each active learning step and (2) learning newly annotated candidates plus a small portion of the misclassified candidates leads to equivalent performance to using the entire labeled set.

Discussion:

How does intra-diversity differ from Inter-diversity: Since measuring diversity between selected samples and unlabeled samples is computationally intractable, especially for a large pool of data, the existing diversity sampling cannot be applied directly to real-world medical applications. To name a few, selection criteria R involves all unlabeled samples (patches). There are 391,200 training patches for polyp detection, and computing their R would demand 1.1 TB memory ($391.00^2 \times 8$). In addition, their algorithms for batch selection are based on the truncated power method, which is unable to find a solution even for the smallest application (e.g., colonoscopy frame classification with 42,000 training patches). Prior known methods cannot be directly used for real-world applications either, as it has a complexity of $O(L^3 \times N^3)$ and requires to train L×N classifiers in each step, where N indicates the number of unlabeled patches and L indicates the number of classes. In addressing the computational complexity problem, the inherent consistency among the patches that are augmented from the same sample is exploited, making it feasible for real-world applications. To contrast these two measures of diversity, the variance among samples refers to inter-diversity, while the variance among patches augmented from the same sample refers to intra-diversity. It is recognized that intra-diversity would inevitably suffer from redundancy in selection, as it treats each sample separately and dismisses inter-diversity among samples. An obvious solution is to inject randomness into active selection criteria (refer to the section entitled "Injecting randomization in active selection"). Nonetheless, a better solution is to combine inter-diversity and intra-diversity together by computing inter-diversity locally on the smaller set of samples selected by intra-diversity. These solutions all aim at selecting sufficiently diverse samples with manageable computational complexity.

Figure 8:
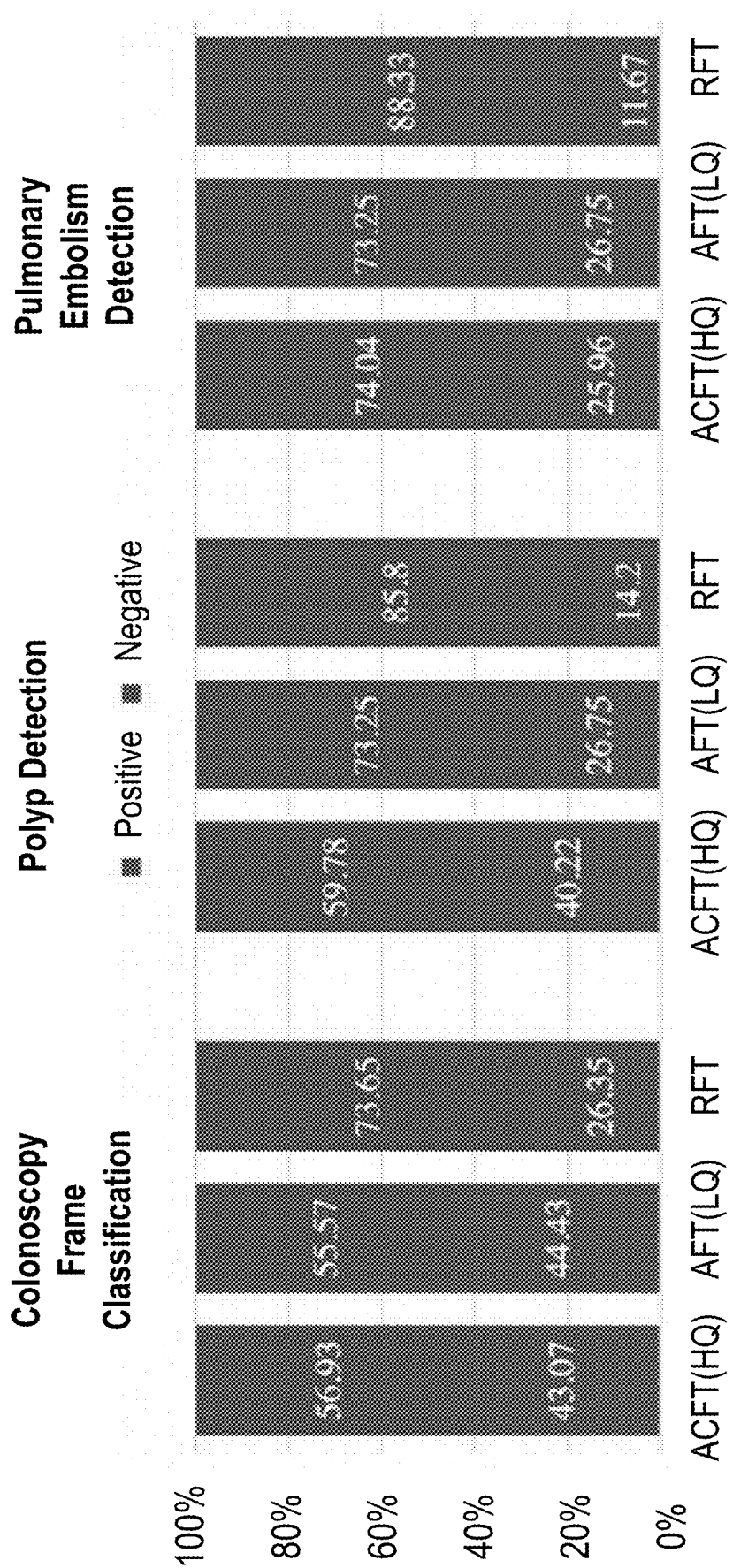
FIG. 8 depicts the positive/negative ratio in the candidates selected by ACFT, AFT, and RFT.

FIG. 8 depicts the positive/negative ratio in the candidates selected by ACFT, AFT, and RFT. Note that the ratio in RFT serves as an approximation for the ratio of the entire dataset.

Can actively selected samples be automatically balanced: Data is often imbalanced in real-world applications. The images of target classes of interest, e.g., certain types of diseases, only appear in a small portion of the dataset. Severe imbalances were encountered in with respect to the three applications. The ratio between positives and negatives was around 1:9 in the polyp and pulmonary embolism detection. Meanwhile, the ratio was approximately 3:7 in the colonoscopy frame classification. Learning from such imbalanced datasets leads to a common issue: majority bias, which is a prediction bias towards majority classes over minority classes. Training data is therefore balanced in terms of classes. Similar to most studies in active learning literature, the described selection criteria are not directly designed to tackle the issue of imbalance, but they have an implicit impact on balancing the data. For instance, when the current CNN has already learned more from positive samples, the next active learning selection would be more likely to prefer those negative samples, and vice-versa. On the contrary, random selection would consistently select new samples that follow roughly the same positive/negative ratio as the entire dataset. As shown here at FIG. 8, the $ACFT_{(HQ)}$ and $AFT_{(LQ)}$ are capable of automatically balancing the selected training data. After monitoring the active selection process, $ACFT_{(HQ)}$ and $AFT_{(LQ)}$ select twice as many positives compared to random selection. This does not suggest that the number of positives and negatives must be approximately identical in the selected samples. Negative samples naturally present more contextual variance than positive ones, as negatives can contain a vast array of possibilities not including the disease of interest. It is expected that the CNN should learn more from negatives to shape the decision boundary of positives. An ideal selection should cover a sufficient variety of negatives while striking an emphasis on the positives. It is believed that this accounts for the quick achievement of superior performance in imbalanced data for the $ACFT_{(HQ)}$ and $AFT_{(LQ)}$ methodologies.

How to prevent model forgetting in continual learning: When a CNN learns from a stream of tasks continually, the learning of the new task can degrade the CNN's performance for earlier tasks. This phenomenon is called catastrophic forgetting. During development of the described methodology and later experimentation, similar behavior was observed in active continual fine-tuning when the CNN encounters newly selected samples. This problem might not arise if the CNN is repeatedly trained on the entire labeled set at every active learning step. But fully reusing the labeled samples is undesirable and wasteful as such training consumes a lot of resources; especially as the labeled set becomes larger and larger, the impact of the newly selected samples on the model training becomes smaller and smaller (relative to the whole labeled set). To make the training more efficient and maximize the contribution of new data, the CNN is fine-tuned only on the newly selected samples, developing the learning strategy called $ACFT_{(Q)}$. However, as seen in Table 4, $ACFT_{(Q)}$ results in a substantially unstable performance because of the catastrophic forgetting. To track the forgotten samples, a histogram was plotted of the misclassified candidates (H) by the current CNN against labeled candidates (L) and newly selected candidates (Q), as presented at FIGS. 9A and 9B. It was found that if the CNN is only fine-tuned on the newly selected samples at each step, it tends to forget the samples that have been learned from previous steps. This is because new data will likely override the weights that have been learned in the past, and thus overfitting the CNN on this data and degrading the model's generalizability. Therefore, the newly selected (Q) and misclassified (H) candidates were combined together to continually fine-tune the current CNN, which not only spotlights the power of new data to achieve the comparable performance (refer again to Table 4: $ACFT_{(HQ)}$ vs. $AFT_{(LQ)}$), but also eases the computational cost by eliminating re-training on easy samples, focusing on hard ones, and preventing catastrophic forgetting.

Figure 9A:
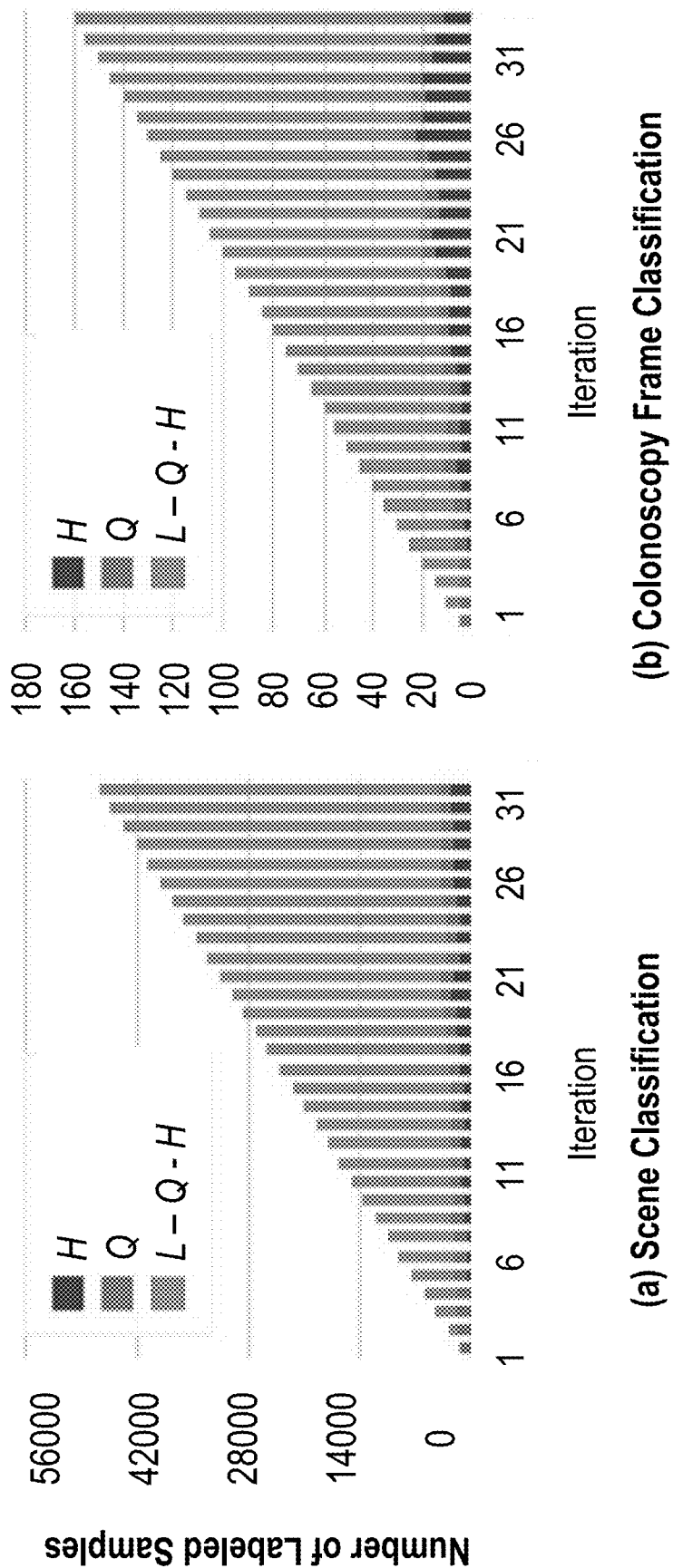
FIGS. 9A and 9B illustrate how labels are reused differently in four active learning strategies, as summarized in Table 2.
Figure 9B:
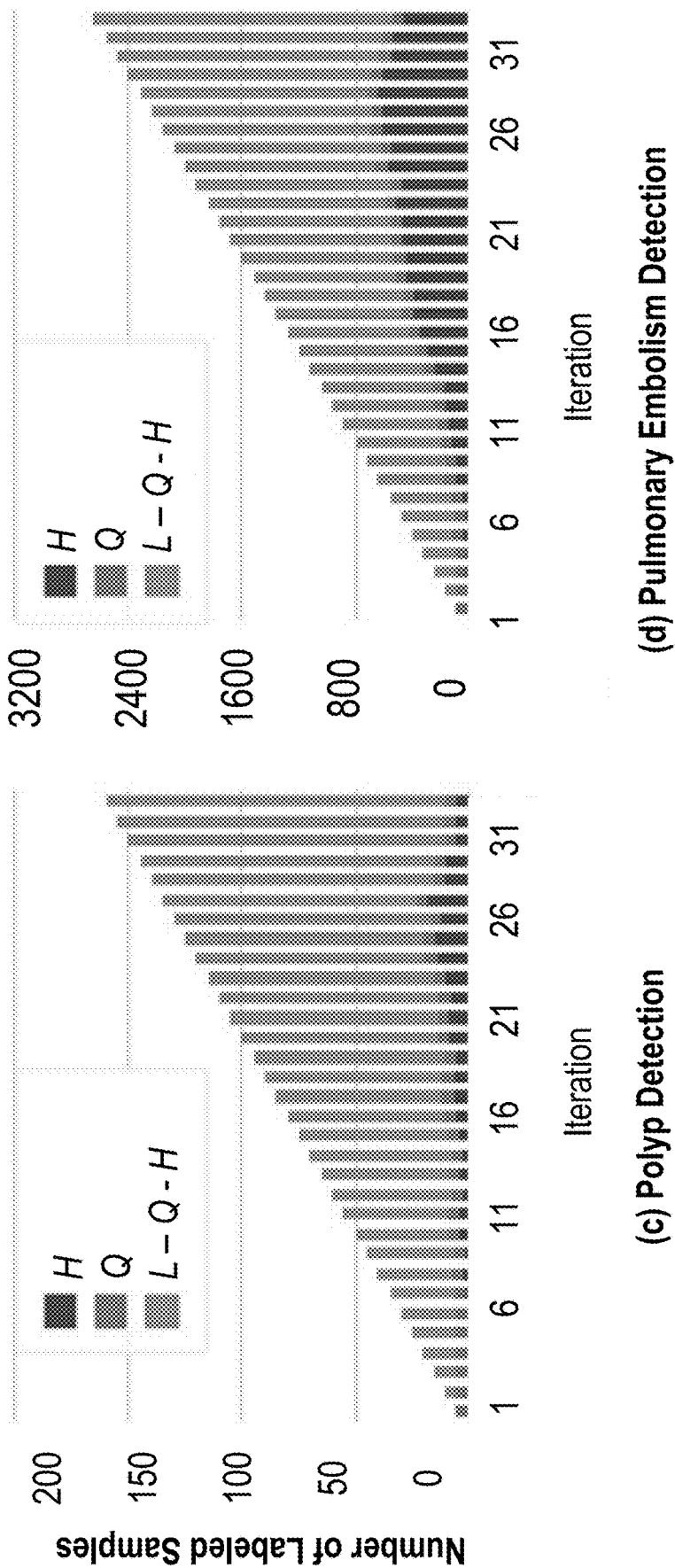

FIGS. 9A and 9B illustrate how labels are reused differently in four active learning strategies, as summarized in Table 2. Specifically, the labels can be non-reused, partially reused, or 100% reused. As depicted, the number of candidates are plotted along with each active learning step, including labeled candidates (L), newly annotated candidates (Q), and misclassified candidates (H). It may therefore be observed that, only by continual fine-tuning on the hybrid data of H∪Q the ACFT significantly reduces training time through faster convergence than repeatedly fine-tuning on the entire labeled data of L∪Q. Most importantly, as evidence by Table 4, partially reusing labels can achieve compelling performance because it boosts performance by eliminating labeled easy candidates, focusing on hard ones, and preventing catastrophic forgetting.

Can actively selected samples be automatically balanced: When a CNN learns from a stream of tasks continually, the learning of the new task can degrade the CNN's performance for earlier tasks. This phenomenon is called catastrophic forgetting. As described herein, similar behavior has been observed in active continual fine-tuning when the CNN encounters newly selected samples. This problem might not arise if the CNN is repeatedly trained on the entire labeled set at every active learning step. But fully reusing the labeled samples takes a lot of resources; further especially when the labeled set gets larger and larger, the impact of the newly selected samples on the model training becomes smaller and smaller (relative to the whole labeled set). To make the training more efficient and maximize the contribution of new data, the inventors attempted to fine-tune the CNN only on the newly selected samples, developing the learning strategy called $ACFT_{(Q)}$. However, as seen in Table 4 (see FIG. 7C), $ACFT_{(Q)}$ results in a substantially unstable performance because of the catastrophic forgetting. To track the forgotten samples, a histogram was plotted of the misclassified candidates (H) by the current CNN against labeled candidates (L) and newly selected candidates (Q) in FIGS. 9A and 9B. It was found that if the CNN is only fine-tuned on the newly selected samples at each step, it tends to forget the samples that have been learned from previous steps. This is because new data will likely override the weights that have been learned in the past, and thus over-fitting the CNN on this data and degrading the model's generalizability. Therefore, the described methodology combines the newly selected (Q) and misclassified (H) candidates together to continual fine-tune the current CNN, which not only spotlights the power of new data to achieve the comparable performance (see Table 4: $ACFT_{(HQ)}$ vs. $AFT_{(LQ)}$), but also eases the computational cost by eliminating re-training on easy samples, focusing on hard ones, and preventing catastrophic forgetting.

Is ACFT generalizable to other models: The experiments were built upon AlexNet and GoogLeNet. Alternatively, deeper architectures, such as VGG, ResNet, DenseNet, and FixEfficientNet, could have been used and they are known to show relatively higher performance for challenging computer vision tasks. However, the purpose of this work is not to achieve the highest performance for different medical image tasks but to answer a critical question: How can annotation costs be significantly reduced when applying CNNs to medical imaging? For this purpose, the inventors experimented with three applications, demonstrating consistent patterns between AlexNet and GoogLeNet as shown in FIGS. 6A, 6B, and 6C. As a result, given this generalizability, the inventors focused on comparing the prediction patterns and learning strategies rather than running experiments on different CNN architectures. Moreover, the active selection criteria only rely on data augmentation and model prediction, without being tied to specific types of predictors. This suggests that not only various CNN architectures, but also other predictive methods—spanning old fashions to recent trends such as CapsuleNet and Transformer—can benefit from the progress in active learning.

Improvement to the cold start problem: It is crucial to intelligently select initial samples for an active learning procedure, especially for algorithms like the ACFT, which starts from a completely empty labeled dataset. The results provided in FIGS. 6A, 6B, and 6C and several other studies reveal that uniformly, randomly selecting initial samples from the unlabeled set could outperform active selection at the beginning. This is one of the most challenging problems in active learning, known as the cold start problem, which is ascribed to (1) data scarcity and (2) model instability at early stages. First, the data distribution in randomly selected samples better reflects the original distribution of the entire dataset than in actively selected samples. Maintaining a similar distribution between training and test data is beneficial when using scarce data. The most common practice is to admit the power of randomness at the beginning and randomly select initial samples from the unlabeled set. The described methodology addresses the cold start problem by incorporating a random sampling probability with respect to the active selection criteria (refer to the section entitled "Injecting randomization in active selection"). The devised ACFT (+randomness vs. −randomness in FIGS. 6A, 6B, and 6C) show superior performance, even in early stages, with continued performance improving during the subsequent steps. Second, in the beginning, the CNN understandably fails to amply predict new samples, as it is trained with an inadequate number of samples. With horrible predictions, no matter how marvelous the selection criterion is, the selected samples would be unsatisfactory—as said "garbage in garbage out" To express meaningful CNN predictions, the use of pre-trained CNNs is recommended (as illustrated in Algorithm 1 at FIG. 1E), not only initializing the CNN at the first step, but also providing fairly reasonable predictions for initial active selection. FIGS. 5A and 5B present encouraging results of active selection using pre-trained CNNs compared with random sampling from the unlabeled set (ACFT vs. RFT). However, a CNN pre-trained on ImageNet may give poor predictions in the medical imaging domain, as it was trained from only natural images; it is associated with a large domain gap for medical images. As a result, the CNN predictions may be inconclusive or even opposite, yielding poor selection scores. Naturally, one may consider utilizing pre-trained models in the same domains to reduce this domain gap has demonstrated this idea in natural language processing by applying self-supervised language modeling to select initial samples. In the case of medical imaging, it is naturally expected that self-supervised methods can also mitigate the pronounced domain gap between natural and medical imaging, offering a great starting point for selecting samples using domain-relevant image representation. More importantly, the learning objectives in self-supervised methods are applicable for discovering the most representative initial samples. For instance, the diversity criterion shares a similar spirit with the learning objective of BYOL and of Parts2Whole, as they all aim to pull together the patches augmented from the same sample. Therefore, their objective functions could serve as an off-the-shelf measure for the power of a sample in elevating the pre-trained CNN's performance. The underlying hypothesis is that the worthiness of labeling a sample correlates with the learning objective of self-supervised pre-training. Specifically, a sample is potentially more worthy to train the CNN if it requires considerably more effort to perform the task of in-painting, restoration, contrastive learning, or colorization. Self-supervised methods are anticipated to have great potential to accommodate the selection of initial samples by leveraging unlabeled data in the same domain, therefore, more effectively addressing the cold start problem in active learning.

Is the observed consistency observation useful for other purposes: One of the key observations is that all patches augmented from the same sample share the same label, and thus are expected to have similar predictions by the CNN. This inherent invariance allows us to devise the diversity metric for estimating the worthiness of labeling the sample. From a broader view, the use of data consistency before and after a mixture of augmentation has played an important role in many other circumstances. In semi-supervised learning, the consistency loss serves as a bridge between labeled and unlabeled data. While the CNN is trained on labeled data, the consistency loss constrains predictions to be invariant to unlabeled data augmented in varying ways. In self-supervised learning, the concept of consistency allows CNNs to learn transformation invariance features by either always restoring the original image from the transformed one or explicitly pulling all patches augmented from the same image together in the feature space. Albeit the great promises of consistency loss, automatic data augmentation inevitably generates "noisy" samples, jeopardizing the data consistency presumption. As an example, when an image contains objects A and B, random cropping may miss either one of the objects fully or partially, causing label inconsistency or representation inconsistency. Therefore, the choice of data augmentation is critical in employing the data consistency presumption. Other than data consistency, the prediction consistency of model ensembles can also calculate the diversity. For instance, prior solutions have proposed to estimate the prediction diversity presented in the CNN via Monte-Carlo dropout in the inference; and yet other solutions measure the prediction consistency by feeding images to multiple independent CNNs that have been trained for the same data and purpose. Unlike the data consistency observed through the experiments described herein, others operate upon a presumption of model consistency, wherein the CNN predictions ought to be consistent if the same sample goes through the model ensembles; otherwise, this sample is considered worthy of labeling.

Figure 10:
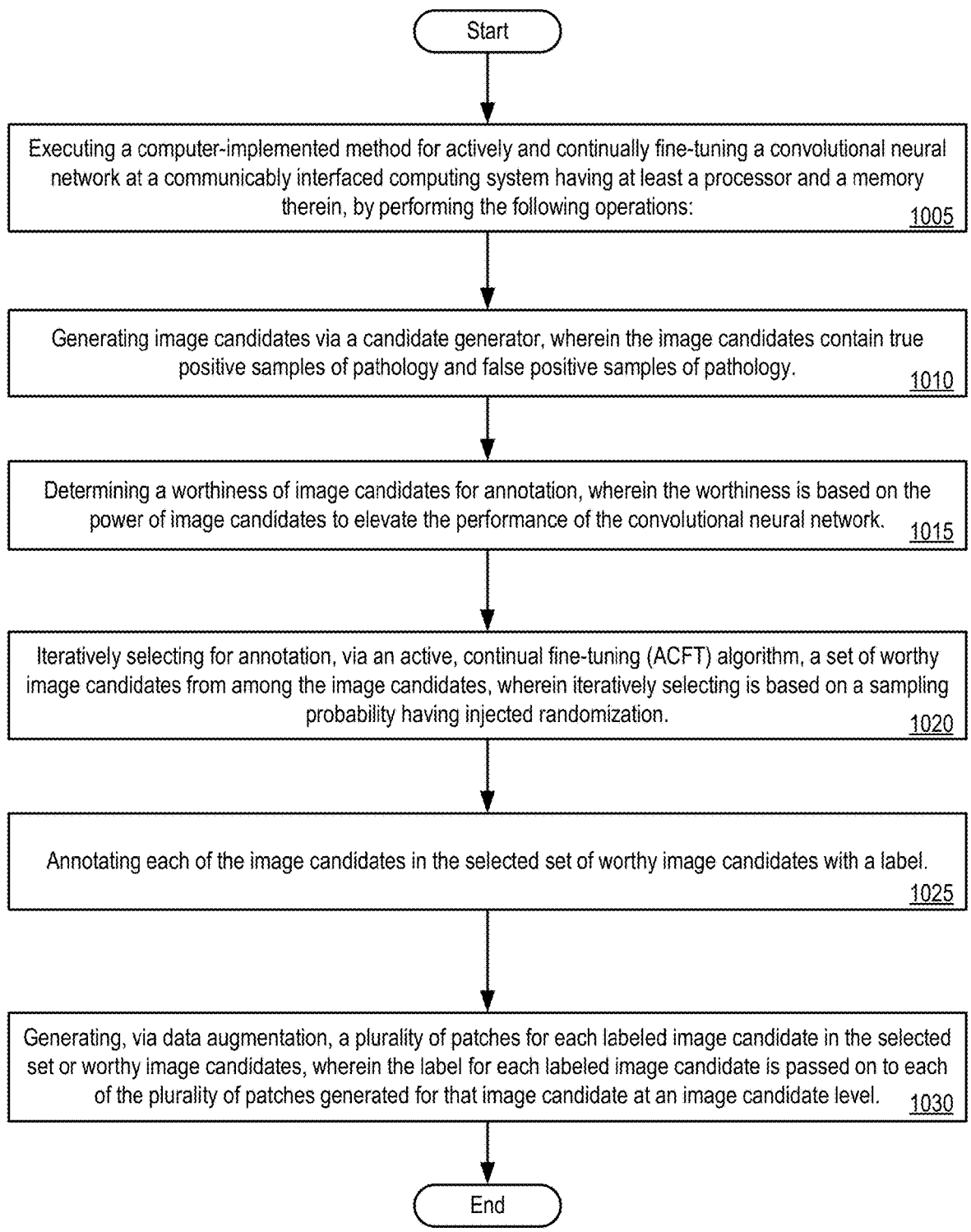
FIG. 10 depicts a flow diagram illustrating a method for actively and continually fine-tuning convolutional neural networks to reduce annotation requirements, in which trained networks are then utilized for the processing of medical imaging, in accordance with disclosed embodiments.

FIG. 10 depicts a flow diagram illustrating a method 1000 for actively and continually fine-tuning convolutional neural networks to reduce annotation requirements, in which trained networks are then utilized for the processing of medical imaging, in accordance with disclosed embodiments. Method 1000 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 1101 (see FIG. 11) and the machine 1201 (see FIG. 12) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 1000 depicted at FIG. 10, there is a method performed by a system specially configured for actively and continually fine-tuning convolutional neural networks to reduce annotation requirements, in which trained networks are then utilized for the processing of medical imaging. Such a system may be configured with at least a processor and a memory to execute specialized instructions which cause the system to perform the following operations:

At block 1005, processing logic of such a system executes a computer-implemented method for actively and continually fine-tuning a convolutional neural network at a communicably interfaced computing system having at least a processor and a memory therein, by performing the operations that follow.

At block 1010, processing logic generates image candidates via a candidate generator, wherein the image candidates contain true positive samples of pathology and false positive samples of pathology.

At block 1010, processing logic determines a worthiness of image candidates for annotation, wherein the worthiness is based on the power of image candidates to elevate the performance of the convolutional neural network.

At block 1020, processing logic iteratively selects for annotation, via an active, continual fine-tuning (ACFT) algorithm, a set of worthy image candidates from among the image candidates, in which the iterative selection operation is based on a sampling probability having injected randomization.

At block 1025, processing logic annotates each of the image candidates in the selected set of worthy image candidates with a label.

At block 1030, processing logic generates, via data augmentation, a plurality of patches for each labeled image candidate in the selected set or worthy image candidates, in which the label for each labeled image candidate is passed on to each of the plurality of patches generated for that image candidate at an image candidate level.

According to another embodiment of method 1000, the power of image candidates to elevate the performance of the convolutional neural network is based on calculating one or more of: (i) entropy (classification certainty), and (ii) diversity (prediction consistency) from among a selected portion of the plurality of patches for each labeled image candidate.

According to another embodiment of method 1000, majority selection is employed to eliminate noisy labels, wherein majority selection involves determining a dominance category for each labeled image candidate and further sorting an output of each of the plurality of patches generated for each labeled image candidate in the convolutional neural network by dominance category.

According to another embodiment of method 1000, the method is applied to a colonoscopy frame classification, wherein an input image is labeled as one or more of: (i) informative, and (ii) non-informative.

According to another embodiment of method 1000, the method is applied to polyp detection to reduce misclassification of polyps based on one or more of variations in: (i) color, (ii) shape, and (iii) size.

According to another embodiment of method 1000, the method is applied to pulmonary embolism detection to improve one or more of: (i) pulmonary embolism diagnosis, and (ii) reading time for CTPA datasets.

According to a particular embodiment, there is a non-transitory computer-readable storage medium having instructions stored thereupon that, when executed by a system having at least a processor and a memory therein, the instructions cause the system to perform operations including: generating image candidates via a candidate generator, wherein the image candidates contain true positive samples of pathology and false positive samples of pathology; determining a worthiness of image candidates for annotation, wherein the worthiness is based on the power of image candidates to elevate the performance of the convolutional neural network; iteratively selecting for annotation, via an active, continual fine-tuning (ACFT) algorithm, a set of worthy image candidates from among the image candidates, wherein iteratively selecting is based on a sampling probability having injected randomization; annotating each of the image candidates in the selected set of worthy image candidates with a label; and generating, via data augmentation, a plurality of patches for each labeled image candidate in the selected set or worthy image candidates, wherein the label for each labeled image candidate is passed on to each of the plurality of patches generated for that image candidate at an image candidate level.

Figure 11:
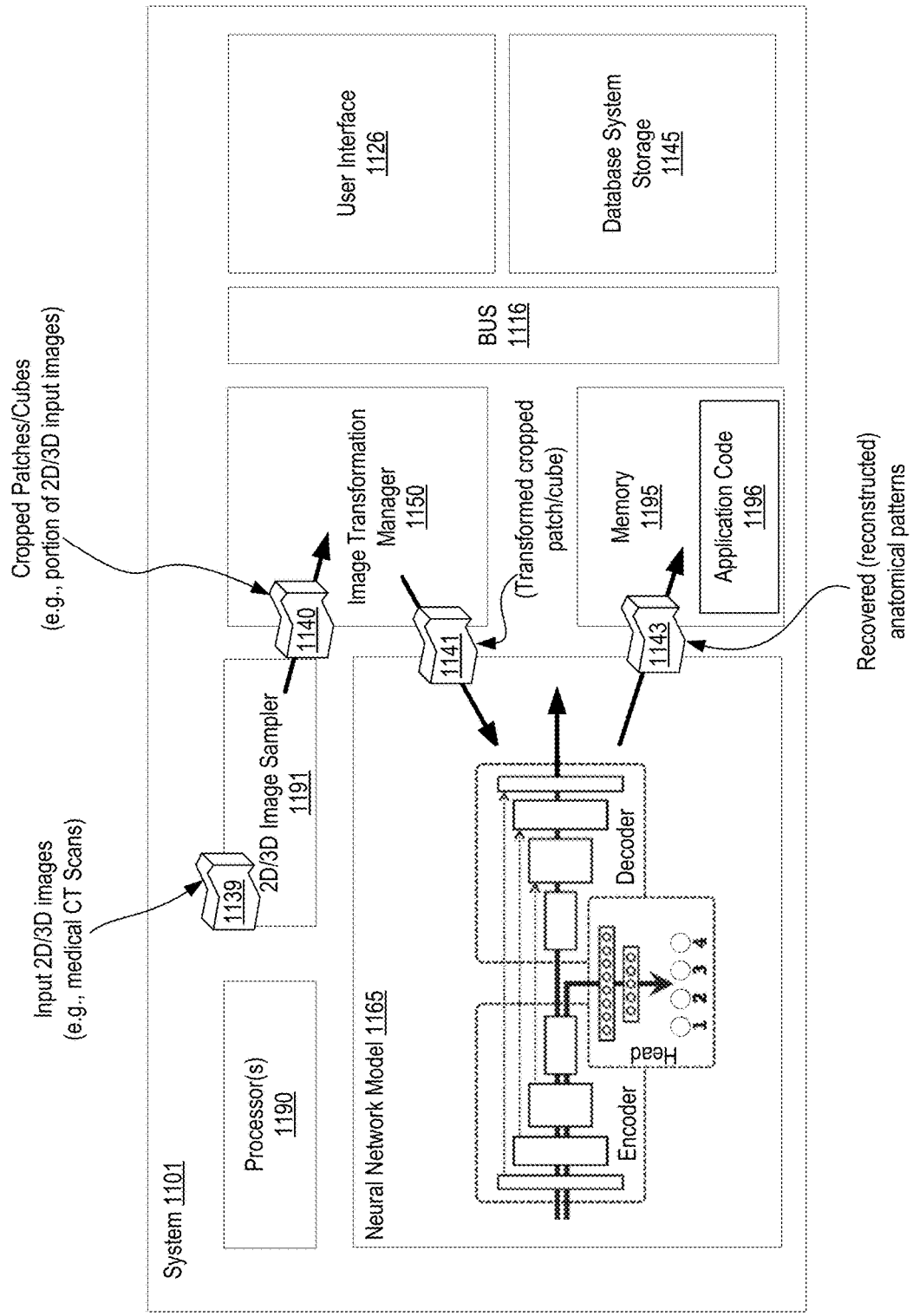
FIG. 11 shows a diagrammatic representation of a system within which embodiments may operate, be installed, integrated, or configured, in accordance with one embodiment.

FIG. 11 shows a diagrammatic representation of a system 1101 within which embodiments may operate, be installed, integrated, or configured. In accordance with one embodiment, there is a system 1101 having at least a processor 1190 and a memory 1195 therein to execute implementing application code 1196. Such a system 1101 may communicatively interface with and cooperatively execute with the benefit of remote systems, such as a user device sending instructions and data, a user device to receive as an output from the system 1101 a semantics-enriched pre-trained model having a trained encoder-decoder structure.

According to the depicted embodiment, the system 1101, includes the processor 1190 and the memory 1195 to execute instructions at the system 1101. The system 1101 as depicted here is specifically customized and configured to actively and continually fine-tuning convolutional neural networks to reduce annotation requirements, in which trained networks are then utilized for the processing of medical imaging, in accordance with disclosed embodiments.

According to a particular embodiment, system 1101 is further configured to execute instructions via the processor for generating image candidates via a candidate generator, wherein the image candidates contain true positive samples of pathology and false positive samples of pathology; determining a worthiness of image candidates for annotation, wherein the worthiness is based on the power of image candidates to elevate the performance of the convolutional neural network; iteratively selecting for annotation, via an active, continual fine-tuning (ACFT) algorithm, a set of worthy image candidates from among the image candidates, wherein iteratively selecting is based on a sampling probability having injected randomization; annotating each of the image candidates in the selected set of worthy image candidates with a label; and generating, via data augmentation, a plurality of patches for each labeled image candidate in the selected set or worthy image candidates, wherein the label for each labeled image candidate is passed on to each of the plurality of patches generated for that image candidate at an image candidate level The model output manager 1185 may further transmit output back to a user device or other requestor, for example, via the user interface 1126, or such information may alternatively be stored within the database system storage 1145 of the system 1101.

According to another embodiment of the system 1101, a user interface 1126 communicably interfaces with a user client device remote from the system and communicatively interfaces with the system via a public Internet.

Bus 1116 interfaces the various components of the system 1101 amongst each other, with any other peripheral(s) of the system 1101, and with external components such as external network elements, other machines, client devices, cloud computing services, etc. Communications may further include communicating with external devices via a network interface over a LAN, WAN, or the public Internet.

Figure 12:
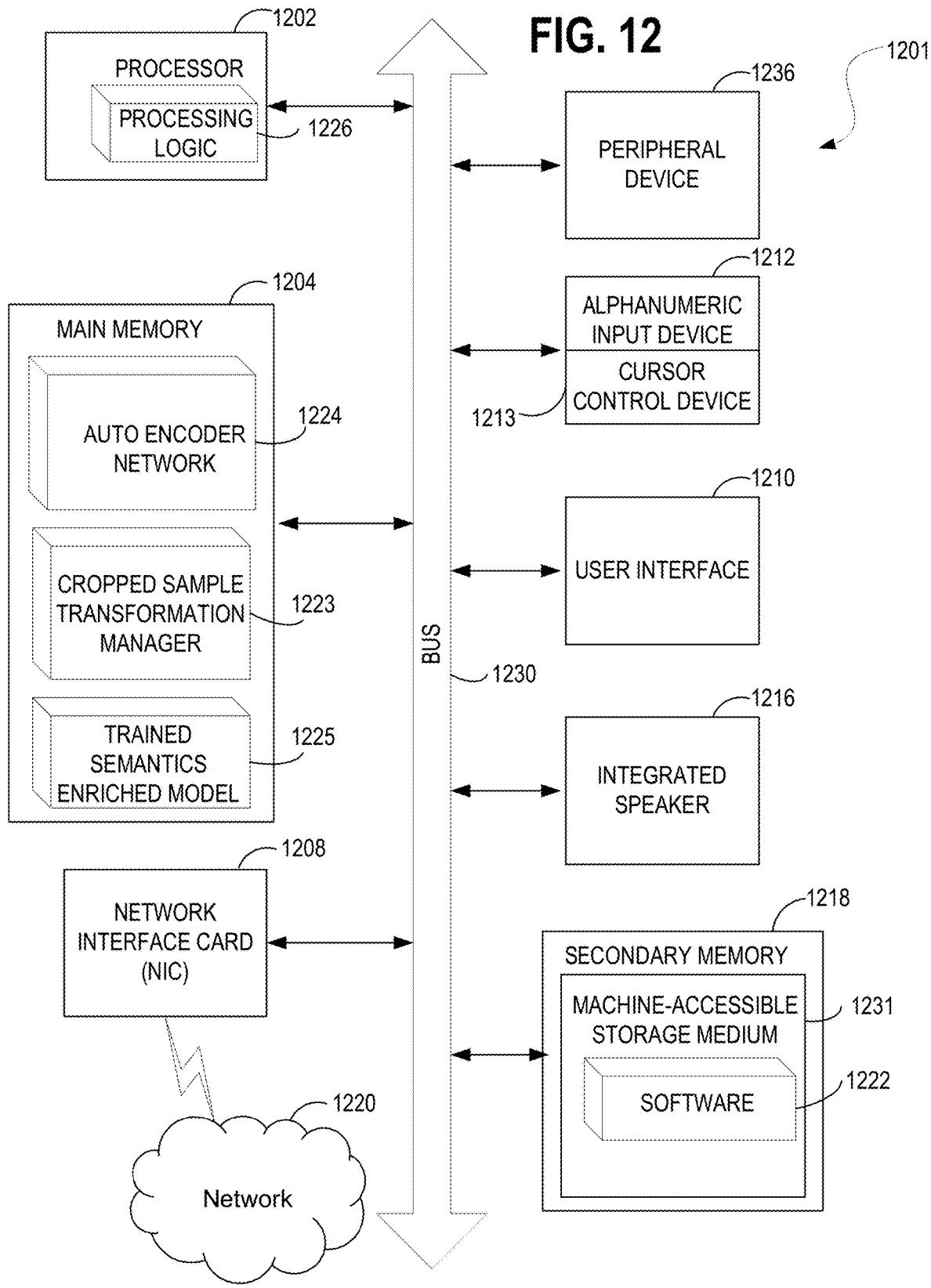
FIG. 12 illustrates a diagrammatic representation of a machine in the exemplary form of a computer system, in accordance with one embodiment.

FIG. 12 illustrates a diagrammatic representation of a machine 1201 in the exemplary form of a computer system, in accordance with one embodiment, within which a set of instructions, for causing the machine/computer system to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1201 includes a processor 1202, a main memory 1204 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 1218 (e.g., a persistent storage device including hard disk drives and a persistent database and/or a multi-tenant database implementation), which communicate with each other via a bus 1230. Main memory 1204 includes an encoder-decoder network 1224 (e.g., such as an encoder-decoder implemented via a neural network model) for performing self-learning operations on transformed 3D cropped samples provided via the cropped sample transformation manager 1223, so as to pre-train an encoder-decoder network within a semantics enriched model 1225 for use with processing medical imaging in support of the methodologies and techniques described herein. Main memory 1204 and its sub-elements are further operable in conjunction with processing logic 1226 and processor 1202 to perform the methodologies discussed herein.

Processor 1202 represents one or more specialized and specifically configured processing devices such as a microprocessor, central processing unit, or the like. More particularly, the processor 1202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1202 may also be one or more special-purpose processing devices such as an application-specific integrated circuit (ASIC), a field programmable gate array (FPGA), a digital signal processor (DSP), network processor, or the like. Processor 1202 is configured to execute the processing logic 1226 for performing the operations and functionality which is discussed herein.

The computer system 1201 may further include a network interface card 1208. The computer system 1201 also may include a user interface 1210 (such as a video display unit, a liquid crystal display, etc.), an alphanumeric input device 1212 (e.g., a keyboard), a cursor control device 1213 (e.g., a mouse), and a signal generation device 1216 (e.g., an integrated speaker). The computer system 1201 may further include peripheral device 1236 (e.g., wireless or wired communication devices, memory devices, storage devices, audio processing devices, video processing devices, etc.).

The secondary memory 1218 may include a non-transitory machine-readable storage medium or a non-transitory computer readable storage medium or a non-transitory machine-accessible storage medium 1231 on which is stored one or more sets of instructions (e.g., software 1222) embodying any one or more of the methodologies or functions described herein. The software 1222 may also reside, completely or at least partially, within the main memory 1204 and/or within the processor 1202 during execution thereof by the computer system 1201, the main memory 1204 and the processor 1202 also constituting machine-readable storage media. The software 1222 may further be transmitted or received over a network 1220 via the network interface card 1208.

Conclusion:

A novel method is therefore described herein which dramatically reduces annotation cost by integrating active learning and transfer learning. Compared with the state-of-the-art random selection method, the described method reduces the annotation cost by at least half for three medical applications and by more than 33% for natural image dataset PLACES-3. The superior performance of the described ACFT methodology is attributable to eight distinct advantages, as described in the introduction. It is therefore believed that labeling at the candidate level offers a sensible balance for three applications, whereas labeling at the patient level would certainly enhance annotation cost reduction, but introduces more severe label noise. Labeling at the patch level compensates for additional label noise but would impose significant burdens on experts for annotation creation.

FIG. 13 illustrates the ideas behind ACFT by utilizing PLACES-3 for scene classification in natural images. For simplicity yet without loss of generality, the experiment was limited to 3 categories: (a) kitchen, (b) living room, and (c) office. PLACES-3 has 15,100 images in each category.

Figure 14A:
FIGS. 14A and 14B provide a gallery of the top five and bottom five candidates actively selected at Step 11 by the methods described herein.
Figure 14B:

FIGS. 14A and 14B provide a gallery of the top five and bottom five candidates actively selected at Step 11 by the methods proposed above (refer to each of the sections labeled "Seeking worthy candidates" and "Handling noisy labels via majority selection") under the experimental setting.

Selected Images Gallery:

Specifically depicted are the top and bottom five images selected by four active selection strategies (i.e., diversity, diversity+majority, entropy and entropy+majority) from PLACES-3 at Step 11 in FIGS. 14A and 14B to create a visual impression of the appearance of newly selected images. Such a gallery offers an intuitive way to analyze the most/least favored images and has helped us develop different active selection strategies.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:
a memory to store instructions;
a processor to execute the instructions stored in the memory;
wherein the system is specially configured to actively and continually fine tune a convolutional neural network by performing the following operations:
generating a plurality of image candidates via a candidate generator, wherein the plurality of image candidates contain true positive samples of pathology and false positive samples of pathology;
determining a worthiness of each of the image candidates for annotation based on one or more of an entropy value and a diversity value calculated for each of a selected number of patches associated with each of the plurality of image candidates;
iteratively selecting for annotation, via an active, continual fine-tuning (ACFT) algorithm, a set of worthy image candidates from among the image candidates, based on the determined worthiness of each of the image candidates for annotation, and according to a sampling probability to inject randomization into the selecting;
annotating each of the image candidates in the selected set of worthy image candidates with a label; and
generating, via data augmentation, a plurality of patches for each labeled image candidate in the selected set of worthy image candidates, wherein the label for each labeled image candidate is applied to each of the plurality of patches associated with that labeled image candidate at an image candidate level.

2. The system of claim 1, further comprising majority selection to determine a dominance category for each labeled image candidate and sort an output of each of the plurality of patches associated with each labeled image candidate in the convolutional neural network by the dominance category.

3. The system of claim 1, wherein the method is applied to a colonoscopy frame classification, wherein an input image is labeled as one or more of: (i) informative, and (ii) non-informative.

4. The system of claim 1, wherein the method is applied to polyp detection to reduce misclassification of polyps based on one or more of variations in: (i) color, (ii) shape, and (iii) size.

5. The system of claim 1, wherein the method is applied to pulmonary embolism detection to improve one or more of: (i) pulmonary embolism diagnosis, and (ii) reading time for CTPA datasets.

6. A computer-implemented method for actively and continually fine-tuning a convolutional neural network, wherein the method comprises:
generating a plurality of image candidates via a candidate generator, wherein the plurality of image candidates contain true positive samples of pathology and false positive samples of pathology;
determining a worthiness of each of the image candidates for annotation based on one or more of an entropy value and a diversity value calculated for each of a selected number of patches associated with each of plurality of image candidates;
iteratively selecting for annotation, via an active, continual fine-tuning (ACFT) algorithm, a set of worthy image candidates from among the image candidates based on the determined worthiness of each of the image candidates for annotation, and according to a sampling probability to inject randomization into the selecting;
annotating each of the image candidates in the selected set of worthy image candidates with a label; and
generating, via data augmentation, a plurality of patches for each labeled image candidate in the selected set of worthy image candidates, wherein the label for each labeled image candidate is applied to each of the plurality of patches associated with that image candidate at an image candidate level.

7. The computer-implemented method of claim 6, further comprising majority selection to determine a dominance category for each labeled image candidate and sort an output of each of the plurality of patches associated with each labeled image candidate in the convolutional neural network by the dominance category.

8. The computer-implemented method of claim 6, wherein the method is applied to a colonoscopy frame classification, wherein an input image is labeled as one or more of: (i) informative, and (ii) non-informative.

9. The computer-implemented method of claim 6, wherein the method is applied to polyp detection to reduce misclassification of polyps based on one or more of variations in: (i) color, (ii) shape, and (iii) size.

10. The computer-implemented method of claim 6, wherein the method is applied to pulmonary embolism detection to improve one or more of: (i) pulmonary embolism diagnosis, and (ii) reading time for CTPA datasets.

11. A non-transitory computer readable storage media having instructions stored thereupon that, when executed by system having at least a processor and a memory therein, the instructions cause the processor to actively and continually fine-tune a convolutional neural network by performing the following operations:
generating a plurality of image candidates via a candidate generator, wherein the plurality of image candidates contain true positive samples of pathology and false positive samples of pathology;
determining a worthiness of each of the image candidates for annotation based on one or more of an entropy value and a diversity value calculated for each of a selected number of patches associated with each of the plurality of image candidates;
iteratively selecting for annotation, via an active, continual fine-tuning (ACFT) algorithm, a set of worthy image candidates from among the image candidates based on the determined worthiness of each of the image candidates for annotation, and according to a sampling probability to inject randomization;
annotating each of the image candidates in the selected set of worthy image candidates with a label; and
generating, via data augmentation, a plurality of patches for each labeled image candidate in the selected set or worthy image candidates, wherein the label for each labeled image candidate is passed on to each of the plurality of patches associated with that image candidate at an image candidate level.

12. The non-transitory computer-readable storage media of claim 11, further comprising majority selection to determine a dominance category for each labeled image candidate and sort an output of each of the plurality of patches generated for each labeled image candidate in the convolutional neural network by dominance category.

13. The non-transitory computer-readable storage media of claim 11, wherein the instructions are configurable to execute a colonoscopy frame classification, wherein an input image is labeled as one or more of: (i) informative, and (ii) non-informative.

14. The non-transitory computer-readable storage media of claim 11, wherein the instructions are configurable to execute a polyp detection to reduce misclassification of polyps based on one or more of variations in: (i) color, (ii) shape, and (iii) size.

15. The non-transitory computer-readable storage media of claim 11, wherein the instructions are configurable to execute a pulmonary embolism detection to improve one or more of: (i) pulmonary embolism diagnosis, and (ii) reading time for CTPA datasets.

* * * * *